(12) United States Patent
Otto et al.

(10) Patent No.: US 8,398,715 B2
(45) Date of Patent: *Mar. 19, 2013

(54) HIGH PERFORMANCE KNEE PROSTHESES WITH CONVERGING ANTERIOR AND POSTERIOR PORTIONS

(75) Inventors: Jason K. Otto, Plantation, FL (US); Brian McKinnon, Bartlett, TN (US); Michael Dean Hughes, Memphis, TN (US); Michael Ries, Tiburon, CA (US); Jan Victor, Brugge (BE); Johan Bellemans, Langdorp (BE); Johnathan Garino, Villanova, PA (US); Timothy Wilton, Duffield (GB)

(73) Assignees: Smith & Nephew, Inc., Memphis, TN (US); The Trustees of The University of Pennsylvania, Philadelphia, PA (US)

( * ) Notice: Subject to any disclaimer, the term of this patent is extended or adjusted under 35 U.S.C. 154(b) by 97 days.

This patent is subject to a terminal disclaimer.

(21) Appl. No.: 12/582,300

(22) Filed: Oct. 20, 2009

(65) Prior Publication Data

US 2010/0042224 A1 Feb. 18, 2010

Related U.S. Application Data

(63) Continuation of application No. 12/023,112, filed on Jan. 31, 2008, now Pat. No. 7,922,771, which is a continuation of application No. 10/743,885, filed on Dec. 22, 2003, now Pat. No. 7,326,252.

(60) Provisional application No. 60/435,426, filed on Dec. 20, 2002.

(51) Int. Cl.
*A61F 2/38* (2006.01)

(52) U.S. Cl. ............... 623/20.14; 623/20.31; 623/20.35

(58) Field of Classification Search ............... 623/20.11, 623/20.14, 20.31, 20.35
See application file for complete search history.

(56) References Cited

U.S. PATENT DOCUMENTS
(Continued)

FOREIGN PATENT DOCUMENTS

| DE | 3314038 A1 | 10/1983 |
| DE | 19529824 A1 | 2/1997 |

(Continued)

OTHER PUBLICATIONS

'European Hospital . . . The European Forum for Those in the Business of Making Healthcare Work,' 12(5/03):1-24 (Oct./Nov. 2003).

(Continued)

*Primary Examiner* — David Isabella
*Assistant Examiner* — Randy Shay
(74) *Attorney, Agent, or Firm* — Kilpatrick Townsend & Stockton LLP

(57) ABSTRACT

Knee prostheses featuring components that more faithfully replicate the structure and function of the human knee joint in order to provide, among other benefits: greater flexion of the knee in a more natural way by promoting or at least accommodating internal tibial rotation in a controlled way, replication of the natural screw home mechanism, and controlled articulation of the tibia and femur respective to each other in a more natural way. In a preferred embodiment, such prostheses include an insert component disposed between a femoral component and a tibial component, the insert component preferably featuring among other things a reversely contoured posterolateral bearing surface that helps impart internal rotation to the tibia as the knee flexes. Other surfaces can also be specially shaped to achieve similar results, preferably using iterative automated techniques that allow testing and iterative design taking into account a manageable set of major forces acting on the knee during normal functioning, together with information that is known about natural knee joint kinetics and kinematics.

33 Claims, 24 Drawing Sheets

U.S. PATENT DOCUMENTS

| | | | |
|---|---|---|---|
| 3,748,662 A | 7/1973 | Helfet | |
| 3,774,244 A | 11/1973 | Walker | |
| 3,798,679 A | 3/1974 | Ewald | |
| 3,816,855 A | 6/1974 | Saleh | |
| 3,924,277 A | 12/1975 | Freeman et al. | |
| 3,958,278 A | 5/1976 | Lee et al. | |
| 4,016,606 A | 4/1977 | Murray et al. | |
| 4,178,641 A | 12/1979 | Grundel et al. | |
| 4,207,627 A | 6/1980 | Cloutier | |
| 4,209,861 A | 7/1980 | Walker et al. | |
| 4,213,209 A | 7/1980 | Insall et al. | |
| 4,249,270 A | 2/1981 | Bahler et al. | |
| 4,340,978 A | 7/1982 | Buechel et al. | |
| 4,353,135 A | 10/1982 | Forte et al. | |
| 4,358,859 A | 11/1982 | Schurman et al. | |
| 4,474,177 A | 10/1984 | Whiteside | |
| 4,524,766 A | 6/1985 | Petersen | |
| 4,568,348 A | 2/1986 | Johnson et al. | |
| 4,586,933 A | 5/1986 | Shoji et al. | |
| 4,653,488 A | 3/1987 | Kenna et al. | |
| 4,659,331 A | 4/1987 | Matthews et al. | |
| 4,662,889 A | 5/1987 | Zichner et al. | |
| 4,703,751 A | 11/1987 | Pohl | |
| 4,711,639 A | 12/1987 | Grundel | |
| 4,714,472 A | 12/1987 | Averill et al. | |
| 4,714,473 A | 12/1987 | Bloebaum | |
| 4,721,104 A | 1/1988 | Kaufman et al. | |
| 4,722,330 A | 2/1988 | Russell et al. | |
| 4,731,086 A | 3/1988 | Whiteside et al. | |
| 4,770,663 A | 9/1988 | Hanslik et al. | |
| 4,787,383 A | 11/1988 | Kenna | |
| 4,822,365 A | 4/1989 | Walker et al. | |
| 4,834,758 A | 5/1989 | Lane et al. | |
| 4,926,847 A | 5/1990 | Luckman | |
| 4,936,853 A | 6/1990 | Fabian et al. | |
| 4,938,769 A | 7/1990 | Shaw | |
| 4,944,757 A | 7/1990 | Martinez et al. | |
| 4,950,297 A | 8/1990 | Ehoy et al. | |
| 4,950,298 A | 8/1990 | Gustilo et al. | |
| 4,963,152 A | 10/1990 | Hofmann et al. | |
| 4,979,949 A | 12/1990 | Matsen, III et al. | |
| 5,002,547 A | 3/1991 | Poggie et al. | |
| 5,007,933 A | 4/1991 | Sidebotham et al. | |
| 5,021,061 A | 6/1991 | Wevers et al. | |
| 5,032,134 A | 7/1991 | Lindwer | |
| 5,047,057 A | 9/1991 | Lawes | |
| 5,053,037 A | 10/1991 | Lackey | |
| 5,062,852 A | 11/1991 | Dorr et al. | |
| 5,071,438 A | 12/1991 | Jones et al. | |
| 5,080,675 A | 1/1992 | Lawes et al. | |
| 5,092,869 A | 3/1992 | Waldron | |
| 5,098,436 A | 3/1992 | Ferrante et al. | |
| 5,100,409 A | 3/1992 | Coates | |
| 5,116,375 A | 5/1992 | Hofmann | |
| 5,122,144 A | 6/1992 | Bert et al. | |
| 5,129,909 A | 7/1992 | Sutherland | |
| 5,133,758 A | 7/1992 | Hollister | |
| 5,133,759 A | 7/1992 | Turner | |
| 5,147,405 A | 9/1992 | Van Zile et al. | |
| 5,147,406 A | 9/1992 | Houston et al. | |
| 5,176,710 A | 1/1993 | Hahn et al. | |
| 5,181,925 A | 1/1993 | Houston et al. | |
| 5,201,881 A | 4/1993 | Evans | |
| 5,203,807 A | 4/1993 | Evans et al. | |
| 5,219,362 A * | 6/1993 | Tuke et al. | 623/20.31 |
| 5,226,916 A | 7/1993 | Goodfellow et al. | |
| 5,228,459 A | 7/1993 | Caspari | |
| 5,234,433 A | 8/1993 | Bert et al. | |
| 5,236,432 A | 8/1993 | Matsen et al. | |
| 5,236,461 A * | 8/1993 | Forte | 623/20.27 |
| 5,250,050 A | 10/1993 | Poggie et al. | |
| 5,263,498 A | 11/1993 | Caspari et al. | |
| 5,282,803 A | 2/1994 | Lackey | |
| 5,282,867 A | 2/1994 | Mikhall | |
| 5,282,870 A | 2/1994 | Moser et al. | |
| 5,304,181 A | 4/1994 | Caspari et al. | |
| 5,314,482 A | 5/1994 | Goodfellow et al. | |
| 5,326,358 A | 7/1994 | Aubriot et al. | |
| 5,330,532 A | 7/1994 | Ranawat | |
| 5,330,533 A | 7/1994 | Walker | |
| 5,330,534 A | 7/1994 | Herrington et al. | |
| 5,336,267 A | 8/1994 | Kubein-Meesenburg et al. | |
| 5,358,527 A | 10/1994 | Forte | |
| 5,358,529 A | 10/1994 | Davidson | |
| 5,358,531 A | 10/1994 | Goodfellows et al. | |
| 5,370,699 A * | 12/1994 | Hood et al. | 623/20.28 |
| 5,370,701 A | 12/1994 | Finn | |
| 5,405,398 A | 4/1995 | Buford, III et al. | |
| 5,413,604 A | 5/1995 | Hodge | |
| 5,417,694 A | 5/1995 | Marik et al. | |
| 5,454,816 A | 10/1995 | Ashby | |
| 5,470,354 A | 11/1995 | Hershberger et al. | |
| 5,480,443 A | 1/1996 | Elias | |
| 5,480,446 A | 1/1996 | Goodfellows et al. | |
| 5,507,820 A | 4/1996 | Pappas | |
| 5,514,143 A | 5/1996 | Bonutti et al. | |
| 5,520,695 A | 5/1996 | Luckman | |
| 5,549,684 A | 8/1996 | Amino et al. | |
| 5,549,686 A * | 8/1996 | Johnson et al. | 623/20.27 |
| 5,549,688 A | 8/1996 | Ries et al. | |
| 5,556,432 A | 9/1996 | Kubein-Meesenburg et al. | |
| 5,609,645 A | 3/1997 | Vinciguerra | |
| 5,611,802 A | 3/1997 | Samuelson et al. | |
| 5,639,279 A | 6/1997 | Burkinshaw et al. | |
| 5,658,342 A | 8/1997 | Draganich et al. | |
| 5,658,344 A | 8/1997 | Hurlburt | |
| 5,667,511 A | 9/1997 | Vendrely et al. | |
| 5,681,354 A * | 10/1997 | Eckhoff | 623/20.35 |
| 5,682,886 A | 11/1997 | Delp et al. | |
| 5,683,468 A | 11/1997 | Pappas | |
| 5,690,635 A | 11/1997 | Matsen et al. | |
| 5,690,637 A | 11/1997 | Wen et al. | |
| 5,702,458 A | 12/1997 | Burstein et al. | |
| 5,723,016 A | 3/1998 | Minns et al. | |
| 5,728,162 A * | 3/1998 | Eckhoff | 623/20.31 |
| 5,738,686 A | 4/1998 | Kubein-Meesenburg et al. | |
| 5,741,259 A | 4/1998 | Chan | |
| 5,755,801 A | 5/1998 | Walker et al. | |
| 5,755,803 A * | 5/1998 | Haines et al. | 623/20.14 |
| 5,755,804 A | 5/1998 | Schmotzer et al. | |
| 5,766,257 A | 6/1998 | Goodman et al. | |
| 5,776,200 A | 7/1998 | Johnson et al. | |
| 5,782,921 A | 7/1998 | Colleran et al. | |
| 5,782,925 A | 7/1998 | Collazo et al. | |
| 5,800,552 A | 9/1998 | Forte | |
| 5,810,824 A | 9/1998 | Chan | |
| 5,810,827 A | 9/1998 | Haines et al. | |
| 5,824,100 A | 10/1998 | Kester et al. | |
| 5,824,102 A | 10/1998 | Buscayret | |
| 5,824,105 A * | 10/1998 | Ries et al. | 623/20.31 |
| 5,871,545 A | 2/1999 | Goodfellows et al. | |
| 5,871,546 A | 2/1999 | Colleran et al. | |
| 5,879,392 A | 3/1999 | McMinn | |
| 5,906,643 A | 5/1999 | Walker | |
| 5,935,173 A | 8/1999 | Roger et al. | |
| 5,954,770 A | 9/1999 | Schmotzer et al. | |
| 5,997,577 A | 12/1999 | Herrington et al. | |
| 6,013,103 A * | 1/2000 | Kaufman et al. | 623/20.15 |
| 6,039,764 A | 3/2000 | Pottenger et al. | |
| 6,056,779 A * | 5/2000 | Noyer et al. | 623/20.32 |
| 6,059,788 A | 5/2000 | Katz | |
| 6,068,658 A | 5/2000 | Insall et al. | |
| 6,080,195 A | 6/2000 | Colleran et al. | |
| 6,086,590 A | 7/2000 | Margulies et al. | |
| 6,099,570 A | 8/2000 | Livet et al. | |
| 6,120,543 A | 9/2000 | Kubein-Meesenburg et al. | |
| 6,123,729 A * | 9/2000 | Insall et al. | 623/20.31 |
| 6,132,468 A | 10/2000 | Mansmann | |
| 6,139,581 A | 10/2000 | Engh et al. | |
| 6,165,223 A | 12/2000 | Metzger et al. | |
| 6,171,340 B1 | 1/2001 | McDowell | |
| 6,190,415 B1 * | 2/2001 | Cooke et al. | 623/20.33 |
| 6,197,064 B1 * | 3/2001 | Haines et al. | 623/20.31 |
| 6,203,576 B1 | 3/2001 | Afriat et al. | |
| 6,205,411 B1 | 3/2001 | DiGiola et al. | |
| 6,206,926 B1 | 3/2001 | Pappas | |
| 6,210,443 B1 | 4/2001 | Marceaux et al. | |

| | | |
|---|---|---|
| 6,235,060 B1 | 5/2001 | Kubein-Meesenburg et al. |
| 6,264,697 B1 | 7/2001 | Walker |
| 6,281,264 B1 | 8/2001 | Salovey et al. |
| 6,306,172 B1 | 10/2001 | O'Neil et al. |
| 6,325,828 B1 | 12/2001 | Dennis et al. |
| 6,361,564 B1 | 3/2002 | Marceaux et al. |
| 6,379,388 B1 | 4/2002 | Ensign et al. |
| 6,406,497 B2 | 6/2002 | Takei |
| 6,413,279 B1 | 7/2002 | Metzger et al. |
| 6,428,577 B1* | 8/2002 | Evans et al. ................ 623/20.29 |
| 6,436,145 B1 | 8/2002 | Miller |
| 6,443,991 B1* | 9/2002 | Running .................... 623/20.27 |
| 6,475,241 B2 | 11/2002 | Pappas |
| 6,485,519 B2 | 11/2002 | Meyers et al. |
| 6,491,726 B2 | 12/2002 | Pappas |
| 6,500,208 B1 | 12/2002 | Metzger et al. |
| 6,506,215 B1 | 1/2003 | Letot et al. |
| 6,547,790 B2 | 4/2003 | Harkey, III et al. |
| 6,554,838 B2 | 4/2003 | McGovern et al. |
| 6,558,426 B1* | 5/2003 | Masini ....................... 623/20.27 |
| 6,569,202 B2 | 5/2003 | Whiteside |
| 6,575,980 B1 | 6/2003 | Robie et al. |
| 6,589,283 B1 | 7/2003 | Metzger et al. |
| 6,620,198 B2 | 9/2003 | Burstein et al. |
| 6,623,526 B1 | 9/2003 | Lloyd |
| 6,645,251 B2 | 11/2003 | Salehi et al. |
| 6,652,587 B2 | 11/2003 | Felt et al. |
| 6,695,848 B2 | 2/2004 | Haines |
| 6,702,821 B2 | 3/2004 | Bonutti |
| 6,730,128 B2 | 5/2004 | Burstein |
| 6,755,864 B1 | 6/2004 | Brack et al. |
| 6,764,516 B2 | 7/2004 | Pappas |
| 6,770,097 B2 | 8/2004 | Leclercq |
| 6,770,099 B2 | 8/2004 | Andriacchi et al. |
| 6,773,461 B2 | 8/2004 | Meyers et al. |
| 6,811,568 B2 | 11/2004 | Minamikawa |
| 6,827,723 B2 | 12/2004 | Carson |
| 6,846,329 B2 | 1/2005 | McMinn |
| 6,866,683 B2 | 3/2005 | Gerbec et al. |
| 6,866,684 B2 | 3/2005 | Fell et al. |
| 6,887,276 B2 | 5/2005 | Gerbec et al. |
| 6,893,467 B1* | 5/2005 | Bercovy .................... 623/20.14 |
| 6,902,582 B2 | 6/2005 | Kubein-Meesenburg et al. |
| 6,911,044 B2 | 6/2005 | Fell et al. |
| 6,916,324 B2 | 7/2005 | Sanford et al. |
| 6,916,340 B2 | 7/2005 | Metzger et al. |
| 6,960,213 B2 | 11/2005 | Chervitz et al. |
| 7,018,418 B2 | 3/2006 | Amrich et al. |
| 7,048,741 B2 | 5/2006 | Swanson |
| 7,066,963 B2 | 6/2006 | Naegeri |
| 7,077,867 B1 | 7/2006 | Pope et al. |
| 7,104,996 B2 | 9/2006 | Bonutti |
| 7,141,053 B2 | 11/2006 | Rosa et al. |
| 7,160,330 B2 | 1/2007 | Axelson, Jr. et al. |
| 7,275,218 B2 | 9/2007 | Petrella et al. |
| 7,326,252 B2 | 2/2008 | Otto et al. |
| 7,364,590 B2 | 4/2008 | Siebel |
| 7,371,240 B2 | 5/2008 | Pinczewski et al. |
| 7,615,082 B2 | 11/2009 | Naegeri et al. |
| 7,922,771 B2 | 4/2011 | Otto et al. |
| 2001/0018615 A1 | 8/2001 | Biegun et al. |
| 2001/0043918 A1 | 11/2001 | Masini et al. |
| 2002/0032450 A1 | 3/2002 | Trudeau et al. |
| 2002/0055784 A1 | 5/2002 | Burstein et al. |
| 2002/0058997 A1 | 5/2002 | O'connor et al. |
| 2002/0103541 A1 | 8/2002 | Meyers et al. |
| 2002/0107576 A1 | 8/2002 | Meyers et al. |
| 2002/0120340 A1 | 8/2002 | Metzger et al. |
| 2002/0161447 A1 | 10/2002 | Salehi et al. |
| 2002/0173852 A1 | 11/2002 | Felt et al. |
| 2002/0177852 A1 | 11/2002 | Chervitz et al. |
| 2002/0177853 A1 | 11/2002 | Chervitz et al. |
| 2003/0009228 A1 | 1/2003 | Meyers et al. |
| 2003/0009230 A1 | 1/2003 | Gundlapalli et al. |
| 2003/0055494 A1 | 3/2003 | Bezuidenhout et al. |
| 2003/0055501 A1 | 3/2003 | Fell et al. |
| 2003/0055509 A1 | 3/2003 | McCue et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0069591 A1 | 4/2003 | Carson et al. |
| 2003/0093156 A1 | 5/2003 | Metzger et al. |
| 2003/0100953 A1 | 5/2003 | Rosa et al. |
| 2003/0153977 A1 | 8/2003 | Suguro et al. |
| 2003/0153978 A1 | 8/2003 | Whiteside |
| 2003/0153979 A1 | 8/2003 | Hughes et al. |
| 2003/0163201 A1 | 8/2003 | McMinn |
| 2003/0220697 A1 | 11/2003 | Justin et al. |
| 2003/0225410 A1 | 12/2003 | Chervitz et al. |
| 2003/0225458 A1* | 12/2003 | Donkers et al. ............ 623/20.15 |
| 2004/0006393 A1 | 1/2004 | Burkinshaw |
| 2004/0030387 A1 | 2/2004 | Landry et al. |
| 2004/0034432 A1 | 2/2004 | Hughes et al. |
| 2004/0044414 A1 | 3/2004 | Nowakowski |
| 2004/0102852 A1 | 5/2004 | Johnson et al. |
| 2004/0122522 A1 | 6/2004 | Kubein-Meesenburg et al. |
| 2004/0143339 A1 | 7/2004 | Axelson, Jr. et al. |
| 2004/0153066 A1 | 8/2004 | Coon et al. |
| 2004/0153164 A1 | 8/2004 | Sanford |
| 2004/0162620 A1 | 8/2004 | Wyss |
| 2004/0193280 A1 | 9/2004 | Webster et al. |
| 2004/0199249 A1 | 10/2004 | Fell |
| 2004/0199250 A1 | 10/2004 | Fell |
| 2004/0204766 A1 | 10/2004 | Siebel |
| 2004/0249467 A1 | 12/2004 | Meyers et al. |
| 2004/0249468 A1 | 12/2004 | Suguro et al. |
| 2004/0267363 A1 | 12/2004 | Fell et al. |
| 2005/0021147 A1 | 1/2005 | Tarabichi |
| 2005/0033424 A1 | 2/2005 | Fell |
| 2005/0055102 A1 | 3/2005 | Tornier et al. |
| 2005/0107886 A1 | 5/2005 | Crabtree et al. |
| 2005/0125069 A1 | 6/2005 | Naegeri et al. |
| 2005/0143832 A1 | 6/2005 | Carson |
| 2005/0171604 A1 | 8/2005 | Michalow |
| 2005/0197710 A1 | 9/2005 | Naegeri |
| 2005/0209701 A1 | 9/2005 | Sugure et al. |
| 2005/0267363 A1 | 12/2005 | Duchon et al. |
| 2005/0267476 A1 | 12/2005 | Chervitz et al. |
| 2006/0015109 A1 | 1/2006 | Haines |
| 2006/0015115 A1 | 1/2006 | Haines |
| 2006/0015116 A1 | 1/2006 | Haines |
| 2006/0015117 A1 | 1/2006 | Haines |
| 2006/0030853 A1 | 2/2006 | Haines |
| 2006/0030854 A1 | 2/2006 | Haines |
| 2006/0030855 A1 | 2/2006 | Haines |
| 2006/0030944 A1 | 2/2006 | Haines |
| 2006/0052875 A1 | 3/2006 | Bernero et al. |
| 2006/0058882 A1 | 3/2006 | Haines |
| 2007/0078517 A1 | 4/2007 | Engh et al. |
| 2008/0119940 A1 | 5/2008 | Otto et al. |
| 2008/0154270 A1* | 6/2008 | Haines et al. ................... 606/88 |
| 2009/0076514 A1 | 3/2009 | Haines |
| 2009/0210066 A1 | 8/2009 | Jasty |
| 2009/0319048 A1 | 12/2009 | Shah et al. |
| 2009/0319049 A1 | 12/2009 | Shah et al. |
| 2010/0076567 A1* | 3/2010 | Justin et al. ................ 623/20.35 |
| 2010/0100192 A1 | 4/2010 | Haines et al. |
| 2010/0185203 A1 | 7/2010 | Haines |
| 2011/0082559 A1 | 4/2011 | Hartdegen et al. |
| 2011/0125280 A1 | 5/2011 | Otto et al. |
| 2011/0125281 A1 | 5/2011 | Otto et al. |
| 2011/0125282 A1 | 5/2011 | Otto et al. |
| 2011/0125283 A1 | 5/2011 | Otto et al. |
| 2011/0130841 A1 | 6/2011 | Otto et al. |
| 2011/0130842 A1 | 6/2011 | Otto et al. |
| 2011/0130843 A1 | 6/2011 | Otto et al. |
| 2011/0137426 A1 | 6/2011 | Otto et al. |
| 2011/0137427 A1 | 6/2011 | Otto et al. |
| 2011/0137619 A1 | 6/2011 | Otto et al. |

FOREIGN PATENT DOCUMENTS

| | | |
|---|---|---|
| EP | 0121142 | 10/1984 |
| EP | 0189253 | 7/1986 |
| EP | 0243109 | 10/1987 |
| EP | 0327249 | 8/1989 |
| EP | 0380451 | 1/1990 |
| EP | 0381352 A1 | 8/1990 |

| | | |
|---|---|---|
| EP | 0 941 719 A2 | 9/1990 |
| EP | 0420460 | 4/1991 |
| EP | 0466659 | 1/1992 |
| EP | 0510299 | 10/1992 |
| EP | 0336774 | 12/1992 |
| EP | 0555003 | 1/1993 |
| EP | 0538153 | 4/1993 |
| EP | 0791338 | 8/1997 |
| EP | 0806920 | 11/1997 |
| EP | 0 916 321 A2 | 5/1999 |
| EP | 0 923 916 A1 | 6/1999 |
| EP | 0 970 667 A1 | 1/2000 |
| EP | 0 988 840 A1 | 3/2000 |
| EP | 1477143 | 11/2004 |
| FR | 2635675 | 3/1990 |
| FR | 2664157 | 1/1992 |
| FR | 2 701 387 | 8/1994 |
| FR | 2 710 258 | 3/1995 |
| FR | 2 760 352 | 9/1998 |
| GB | 1 409 150 | 10/1975 |
| GB | 2007980 | 7/1982 |
| GB | 2 296 443 A | 7/1996 |
| GB | 2 324 249 A | 10/1998 |
| GB | 2 335 145 A | 9/1999 |
| JP | 61170453 | 8/1986 |
| JP | 62133948 | 6/1987 |
| JP | 62254750 | 11/1987 |
| JP | 02246971 | 10/1990 |
| JP | 0315460 | 1/1991 |
| JP | 04297254 | 10/1992 |
| JP | 05041510 | 6/1993 |
| JP | 06237941 | 8/1994 |
| JP | 11504226 | 2/1996 |
| JP | 2001524349 | 6/1999 |
| JP | 11313845 | 11/1999 |
| JP | 2000116682 | 4/2000 |
| JP | 2000201955 | 7/2000 |
| JP | 2000312691 | 11/2000 |
| JP | 2002224149 | 8/2002 |
| RU | 2121319 | 11/1998 |
| WO | WO91/10408 | 7/1991 |
| WO | WO93/03681 | 3/1993 |
| WO | WO93/22990 | 11/1993 |
| WO | WO93/25157 | 12/1993 |
| WO | WO94/05212 | 3/1994 |
| WO | WO94/09730 | 5/1994 |
| WO | WO 9422397 | 10/1994 |
| WO | WO94/28812 | 12/1994 |
| WO | WO95/03003 | 2/1995 |
| WO | WO96/01087 | 1/1996 |
| WO | WO96/01588 | 1/1996 |
| WO | 9603939 | 2/1996 |
| WO | WO96/03097 | 2/1996 |
| WO | WO96/23460 | 8/1996 |
| WO | WO96/24311 | 8/1996 |
| WO | WO97/29703 | 8/1997 |
| WO | WO97/29704 | 8/1997 |
| WO | WO98/20817 | 5/1998 |
| WO | 9927872 | 6/1999 |
| WO | WO 99/27872 | 6/1999 |
| WO | WO 99/30649 | 6/1999 |
| WO | WO 01/13825 | 3/2001 |
| WO | WO2004/100839 | 11/2004 |

OTHER PUBLICATIONS

Office Action dated Dec. 21, 2011 in related Australian Patent Application No. 2010200901.
Office Action dated Aug. 17, 2011 in related U.S. Appl. No. 12/952,667.
Office Action dated Aug. 19, 2011 in related U.S. Appl. No. 12/952,779.
Office Action dated Aug. 25, 2011 in related U.S. Appl. No. 12/952,859.
Office Action dated Aug. 17, 2011 in related U.S. Appl. No. 12/952,611.
Office Action dated Aug. 17, 2011 in related U.S. Appl. No, 12/952,704.
Office Action dated Aug. 11, 2011 in related U.S. Appl. No. 12/952,648.
Office Action dated Jun. 7, 2011 in related U.S. Appl. No. 12/952,584.
Office Action dated Jul. 11, 2011 in related U.S. Appl. No. 12/952,625.
Office Action dated Sep. 16, 2011 in related U.S. Appl. No. 12/971,623.
Office Action dated Oct. 24, 2011 in related U.S. Appl. No. 12/971,507.
Australian Office Action dated Oct. 14, 2011 in related Application No. 2010200901.
Office Action dated Mar. 27, 2007 in related U.S. Appl. No. 10/743,885.
Notice of Allowance dated Sep. 13, 2007 in related U.S. Appl. No. 10/743,885.
Office Communication dated Mar. 21, 2012 in related European Patent Application No. 10012160.7.
Office Action dated Jun. 19, 2012 in related Japanese Application No. 2010-152060.
Office Action dated Jul. 20, 2012 in U.S. Appl. No. 12/952,648.
Office Action dated Jul. 10, 2012 in U.S. Appl. No. 12/952,625.
Office Action dated Jul. 20, 2012 in U.S. Appl. No. 12/952,584.
Office Action dated Jul. 20, 2012 in U.S. Appl. No. 12/971,507.
Office Action dated Jul. 20, 2012 in U.S. Appl. No. 12/971,623.
Office Action dated Jul. 10, 2012 in U.S. Appl. No. 12/952,667.
Office Action dated Jul. 20, 2012 in U.S. Appl. No. 12/952,611.
Office Action dated Jul. 3, 2012 in U.S. Appl. No. 12/952,779.
Office Action dated Jul. 20, 2012 in U.S. Appl. No. 12/952,859.
Office Action dated Jul. 20, 2012 in U.S. Appl. No. 12/952,704.
Whiteside Ortholoc Total Knee System: Surgical Procedure, Dow Corning Wright, pp. WMT000001-WMT000040, Jun. 1985.
Zimmer, Insall/Burstein II Constrained Condylar: Modular Knee System, Surgical Technique, copyright 1989.
Exhibits 4, 5 and 8 from *Hudson Surgical Design, Inc. v. Zimmer Holdings, Inc., Zimmer Inc., Rush System for Health and Rush University Medical Center*, Hudson Surgical Design, Inc.'s Opening Brief on Claim Construction Case No. 1:08-cv-01566, Civil Action No. 08C1566, Document No. 83, filed Nov. 17, 2008, 6 pages.
*Hudson Surgical Design v. Zimmer Holdings, Inc., et al.*, Revised Final Claim Construction Chart, filed Mar. 11, 2009, 18 pages.
Haines et al., Accelerated Examination Search Statement and Support Document for Femoral Prosthetic Implant from U.S. Appl. No. 12/638,692, dated Dec. 15, 2009, 85 pages.
Office Action for U.S. Appl. No. 12/638,692, mailed Oct. 22, 2010, 19 pages.
Supplemental Information Disclosure Statement filed in U.S. Appl. No. 12/638,692, on Nov. 16, 2010, 19 pages.
Haines et al., Correct Accelerated Examination Search Statement and Support Document for Femoral Prosthetic Implant from U.S. Appl. No. 12/757,778 dated Apr. 9, 2010, 104 pages.
Office Action for U.S. Appl. No. 11/933,298, mailed Dec. 2, 2010, 20 pages.
Freeman, Samuelson, Total Knee System, Biomet, Inc., 1994, attached as Exhibit F, 60 pages.
Freeman, M.A.R., and Samuelson, K.M., Protek® Mark II Total Knee Replacement System, published 1985, 21 pages, attached as Exhibit G.
Protek F/S Modular Total Knee Replacement System, published by Protek, Jan. 1991, pp. 1-58, attached as Exhibit H.
Buechel, F.F., et al., "Low Contact Stree Meniscal Bearing Unicompartmental Knee Replacement : Long-Term Evaluation of Cemented and Cementless Results," Journal of Orthopaedic Rheumatology, presented at the 57th Annual American Academy of Orthopaedic Surgeons Meeting, New Orleans, LA, Feb. 11, 1990, Bates No. DEP00004096-DEP00004107, 13 pages.
N.J. Unicompartmental Knee, Sep. 15, 1989, Bates No. DEP00004108-DEP00004116, 10 pages.
Buechel, F.F., "NJ LCS Unicompartmental Knee System with Porocoat: Surgical Procedure," Oct. 24, 1994, Bates No. DEP00004117-DEP00004130, 15 pages.
Buechel, F.F., NJ LCS Unicompartmental Knee System with Proocoat, 1994, Bates No. DEP00004142-DEP4152, 11 pages.

Engh, G.A., et al., "The AMK Total Knee System, Design Rationale and Surgical Procedure," Published by DePuy, 1989, Bates No. DEP00004153-DEP00004201, 50 pages.

Chapman, Michael, W., ed., "Primary Total Knee Arthroplasty," Operative Orthopaedics, vol. 1, published by J.B. Lippincott Co., Philadelphia, 1988, pp. 719-725 and p. 86, Bates No. DEP00004236-DEP00004247.

Crossett, L.S., et al., 'AMK Congruency Instrument System, Surgical Technique,' published by DePuy, 1997, Bates No. DEP00004252-DEP00004267, 17 pages.

Engh, G.A., et al., 'AMK Surgical Technique,' published by DePuy, 1989, Bates No. DEP00004299-DEP00004329, 32 pages.

Desjardins, D., et al., 'Interax Operative Techniques,' Interax, 1994, Bates No. DEP00004391-DEP00004411, 22 pages.

Desjardins, D., et al., 'Interax Total Knee Operative Technique,' Interax, 1993, Bates No. DEP00004412-DEP00004432, 22 pages.

Baird, et al., LCS Uni : Unicompartmental Knee System with Porocoat, >> published by DePuy, 1991, Bates No. DEP00004452-DEP00004462, 12 pages.

Oxford Meniscal Knee Phase II Unicompartmental Replacement, published by Biomet prior to Jun. 7, 1994, Bates No. DEP00004509-DEP00004515, 8 pages.

Scott, R.D., et al., 'P.F.C. Signa Uni-compartmental Knee System,' published by Johnson & Johnson, 1998, Bates No. DEP00004531-DEP00004539, 10 pages.

Scott, R.D., et al., 'Unicondylar Unicompartmental Replacement for Osteoarthritis of the Knee,' Journal of Bone and Joint Surgery, vol. 63-A, No. 4, Apr. 1, 1981, pp. 536-544, Bates No. DEP00004764-DEP00004775.

Office Action for U.S. Appl. No. 12/757,778, mailed Nov. 15, 2010, 17 pages.

U.S. Appl. No. 12/952,648, filed Nov. 23, 2010.
U.S. Appl. No. 12/952,625, filed Nov. 23, 2010.
U.S. Appl. No. 12/952,584, filed Nov. 23, 2010.
U.S. Appl. No. 12/952,667, filed Nov. 23, 2010.
U.S. Appl. No. 12/952,779, filed Nov. 23, 2010.
U.S. Appl. No. 12/952,859, filed Nov. 23, 2010.
U.S. Appl. No. 12/952,611, filed Nov. 23, 2010.
U.S. Appl. No. 12/952,704, filed Nov. 23, 2010.
U.S. Appl. No. 12/971,623, filed Dec. 17, 2010.
U.S. Appl. No. 12/971,507, filed Dec. 17, 2010.

Ad-hoc press release 2$^{nd}$ Oct. 2002, 2 pages http://www.aap.de/VirtuelleHosts/aap/en/Investor/News/Newsarchiv_2002/AH_02.10.2002 Accessed Jun. 13, 2006.

Mebio Knee, one page, 2006 http://www.aap.de/en/Produkte/Endoprothetik/Knieendoprothetic/Mebio_Knie/index_html Accessed Jun. 13, 2006.

Essinger, et al., "A Mathematical Model for the Evaluation of the Behaviour During Flexion of Condylar-Type Knee Prosthesis," J. Biomechanics, 22:1229-1241 (1989).

Stiehl, et al., "In Vivo Kinematic Analysis of a Mobile Bearing Total Knee Prosthesis," Clinical Orthopaedics and Related Research, 345:60-66 (1997).

Kim, et al., "Rollback in Porterior Cruciate Ligament-retaining Total Knee Arthroplasty," The Journal of Arthroplasty, 12(5):553-561 (1997).

Matsuda, et al., "Knee Kinematics of Posterior Cruciate Ligament Sacrificed Total Knee Anthroplasty," Clinical Orthopaedics and Related Research, 341:257-266 (1997).

Szivek, et al., "Average and Peak Contant Stress Distribution Evaluation of Total Knee Arthroplasties," The Journal of Arthroplasty, 11(8):952-963 (1996).

Dennis, et al., "In Vivo Knee Kinematics Derived Using an Inverse Perspective Technique," Clinical Orthopaedics and Related Research, 331:107-117 (1996).

Sathasivam, et al., "Optimization of the Bearing Surface Geometry of Total Knees," J. Biomechanics, 27(3):255-264 (1994).

Office Action dated Oct. 27, 2009 in U.S. Appl. No. 12/023,112.
Response dated Mar. 1, 2010 in U.S. Appl. No. 12/023,112.
Office Action dated May 10, 2010 in U.S. Appl. No. 12/023,112.
Response dated Aug. 4, 2010 in U.S. Appl. No. 12/023,112.
Notice of Allowance date Dec. 17, 2010 in U.S. Appl. No. 12/023,112.
Notice of Allowance dated Feb. 16, 2010 in U.S. Appl. No. 12/023,112.
Office Action dated Nov. 9, 2012 in U.S. Appl. No. 12/952,625.
Notice of Allowance dated Nov. 8, 2012 in U.S. Appl. No. 12/952,667.
Office Action dated Nov. 5, 2012 in U.S. Appl. No. 12/952,779.
Office Action dated Nov. 1, 2012 in U.S. Appl. No. 12/952,859.
Notice of Allowance dated Nov. 8, 2012 in U.S. Appl. No. 12/952,584.
Notice of Allowance dated Dec. 14, 2012 in U.S. Appl. No. 12/952,704.
Notice of Allowance dated Nov. 30, 2012 in U.S. Appl. No. 12/952,648.
Office Action dated Jan. 16, 2013 in U.S. Appl. No. 12/971,507.
Notice of Allowance dated Jan. 22, 2013 in U.S. Appl. No. 12/952,611.
Office Action dated Jan. 22, 2013 in U.S. Appl. No. 12/971,623.

* cited by examiner

HIGH PERFORMANCE KNEE PROSTHESES WITH CONVERGING ANTERIOR AND POSTERIOR PORTIONS

CROSS-REFERENCE TO RELATED APPLICATIONS

This application is a continuation application of U.S. patent application Ser. No. 12/023,112 filed Jan. 31, 2008, which is a continuation application of U.S. patent application Ser. No. 10/743,885 filed Dec. 22, 2003, now patented as U.S. Pat. No. 7,326,252, which application claims priority to U.S. Ser. No. 60/435,426 entitled "Knee Prosthesis Having Improved Stability and Rotational Control" filed Dec. 20, 2002, the entire contents of all of which are herein incorporated by this reference.

BACKGROUND

1. Field of the Invention

The invention relates generally to knee prostheses and, more specifically, to knee prostheses which more closely emulate the anatomy and function of the knee and thereby feature range of flexion, rotation of the tibia relative to the femur, the screw home mechanism, and other structural and functional characteristics of the actual knee joint.

2. General Background of the Invention

Disease and trauma affecting the articular surfaces of the knee joint are commonly treated by surgically replacing the ends of the femur and tibia with prosthetic femoral and tibial implants, and, in some cases, replacing the patella with a patella component. Such surgeries are sometimes referred to as total knee replacement (TKR). In TKR surgery, a surgeon typically affixes two prosthetic components to the patient's bone structure; a first to the patient's femur and a second to the patient's tibia. These components are typically known as the femoral component and the tibial component respectively.

The femoral component is placed on a patient's distal femur after appropriate resection of the femur. The femoral component is usually metallic, having a highly polished outer condylar articulating surface, which is commonly J-shaped.

A common type of tibial component uses a tray or plateau that generally conforms to the patient's resected proximal tibia. The tibial component also usually includes a stem that extends at an angle to the plateau in order to extend into a surgically formed opening in the patient's intramedullary canal. The tibial component and tibial stem are both usually metallic.

A plastic or polymeric (often ultra high molecular weight polyethylene) insert or bearing fits between the tray of the tibial component and the femoral component. This insert provides a surface against which the femoral component condylar portion articulates, i.e., moves in gross motion corresponding generally to the motion of the femur relative to the tibia.

Modern TKR's are tricompartmental designs; they replace three separate articulating surfaces within the knee joint: the patello-femoral compartment and the lateral and medial inferior tibio-femoral compartments. Most currently available TKR's are designed to articulate from a position of slight hyperextension to approximately 115 to 130° flexion. A tricompartmental design can meet the needs of most TKR patients even though the healthy human knee is capable of a range of motion (ROM) approaching 170°. However, there are some TKR patients who have a particular need to obtain high flexion in the knee joint. For many, a TKR that permits patients to achieve a ROM in excess of 130° is desirable to allow deep kneeling, squatting and sitting on the floor with the legs tucked underneath.

Additionally, a common complaint of TKR patients is that the replaced knee does not does function like a normal knee or "feel normal." The replaced knee does not achieve normal knee kinematics or motion and generally has a more limited ROM than a normal knee. Currently available designs produce kinematics different than the normal knee during gait, due to the complex nature of the knee joint and the motion of the femur and tibia relative to one another during flexion and extension. For example, it is known that, in addition to rotating about a generally horizontal axis during flexion and extension, the tibia also rotates about its longitudinal axis. Such longitudinal rotation is typically referred to as either external or internal rotation, depending on whether reference is being made to the femur or tibia respectively.

Very few currently available designs allow this longitudinal rotation. One known method to allow rotation is a mobile-bearing knee prosthesis. In mobile-bearing knee prostheses, the insert has increased contact with the condyles of the femoral component and rotates on top of the tibial component. However, mobile-bearing knee prostheses are less forgiving of soft tissue imbalance, increasing the incidence of bearing spin-out and dislocation. Another concern is that the mobile-bearing prostheses create an additional interface and underside wear may occur.

Constructing a total knee prosthesis which replicates the kinematics of a natural knee has been an on-going challenge in the orthopaedic field. Several attempts have been made and are well known in the prior art, including those shown in U.S. Pat. Nos. 6,264,697 and 6,325,828. Conventional designs such as these, however, leave room for improvement in simulating the structure and operation of actual knee joints, in at least the aspects of range of motion, internal rotation of the tibia relative to the femur as the knee flexes, and rotation of the tibia relative to the femur in overextension in order to allow the knee to be stabilized more efficiently.

SUMMARY

Devices according to aspects of the invention achieve more faithful replication of the structure and function of the actual knee joint by, among other things, adoption and use of structure and shaping of at least the polymeric insert and the femoral component to cause these components to cooperate with each other in new and unconventional ways (at least in the art of prosthetics) at various stages throughout the range of knee motion.

According to certain aspects and embodiments of the invention, there is provided a knee prosthesis in which the insert features a lateral posterior surface which slopes in a distal direction (as compared to the corresponding medial posterior surface) as it continues toward the posterior aspect of the insert, in order to cooperate with the lateral condyle of the femoral component to impart internal rotation to the tibia as the knee flexes between substantially 0 and substantially 130 degrees of flexion, to allow the prosthesis to induce or allow tibial internal rotation in a controllable manner as a function of flexion, to reduce the forces of any femoral component cam acting upon a post or other raised portion of the insert, or any combinations of these.

According to certain aspects and embodiments of the invention, there is further provided a knee prosthesis in which the insert features a greater thickness in certain lateral portions to increase durability, accommodate a more anatomic femoral component which features a lateral condyle smaller in some dimensions than its medial condyle, to impart a joint line more accurately replicating natural physiology, or any combinations of these.

According to certain aspects and embodiments of the invention, there is further provided a knee prosthesis in which the insert features more anatomic sulcus placement in order improve operation of the prosthesis by more anatomically applying forces imposed on the prosthesis by quadriceps and the patellar tendon, allow the prosthesis to replicate natural anatomy more effectively, or any combinations of these.

According to certain aspects and embodiments of the invention, there is further provided a knee prosthesis in which the insert features a lateral surface that is curved or "swept" in plan, in order to allow the lateral condyle to track in arcuate fashion on the bearing surface at certain ranges of knee flexion and rotation, to assist in facilitating the screw home mechanism, or combinations of these.

According to certain aspects and embodiments of the invention, there is further provided a knee prosthesis in which the insert features a post or other raised portion whose anterior surface is shaped to serve effectively as an anterior cruciate ligament when engaged with a cam during ranges of flexion such as after heel strike upon actuation of the quadriceps.

According to certain aspects and embodiments of the invention, there is further provided a knee prosthesis in which the insert features a post or other raised portion whose posterior surface is shaped to assist internal rotation of the tibia relative to the femur as the knee flexes, such as starting at angles such as in a range of substantially 50 or more degrees, to help ensure that post/cam forces are directed net anteriorly, or a combination of these.

According to certain aspects and embodiments of the invention, there is further provided a knee prosthesis in which the insert features rounded or chamfered peripheral edges to help reduce wear on surrounding tissue and/or for other purposes.

According to certain aspects and embodiments of the invention, there is further provided a knee prosthesis with any desired combination or permutation of any of the foregoing features, properties or results.

According to certain aspects and embodiments of the invention, there is further provided a knee prosthesis including a femoral component that includes a lateral condyle that is in some distal and posterior aspects smaller than corresponding dimensions of the medial condyle, in order to simulate more closely natural physiology, allow adequate insert thickness under the lateral condyle so that, for instance, the posteriolateral surface of the insert can feature convexity or slope, assist internal rotation of the tibia relative to the femur as the knee flexes from substantially 0 degrees to substantially 130 degrees, or any combinations of these.

According to certain aspects and embodiments of the invention, there is further provided a knee prosthesis including a femoral component that includes a lateral condyle with anterior surfaces more pronounced than corresponding anterior surfaces on the medial condyle, in order to replicate more closely natural anatomic structures in retaining the patella in lower ranges of flexion, cause the patella or substitute structure to track more physiologically at such ranges of motion, cause the quadriceps more physiologically to apply force to the prosthetic components and tibia in lower ranges of flexion, or any combinations of these.

According to certain aspects and embodiments of the invention, there is further provided a knee prosthesis including a femoral component that includes a cam that cooperates with a post or other raised portion on the insert to assist internal rotation on the tibia, ensure that cam/post forces are directed net anteriorly or a combination of these.

According to certain aspects and embodiments of the invention, there is further provided a knee prosthesis including a femoral component that includes an anterior cam which cooperates with a post or other raised portion on the insert to simulate action of the anterior cruciate ligament at lower ranges of flexion.

According to certain aspects and embodiments of the invention, there is further provided a knee prosthesis including a femoral component and an insert in which during operation in situ, the femoral component is situated more anteriorly on the insert at low angles of flexion than in conventional knee prostheses, in order to reduce the forces on the post of the insert, to resemble more closely actual operation and kinematics of the knee, or a combination of these.

According to certain aspects and embodiments of the invention, there is further provided a knee prosthesis including a femoral component and an insert which during operation in situ reduces paradoxical motion and actual cam to post contact, and when there is contact, reduces impact of contact and force of contact, between the femoral component cam and the insert post or other raised portion during desired ranges of motion.

According to certain aspects and embodiments of the invention, there is further provided a knee prosthesis including a femoral component which features a backdrafted anterior slope of the interior surfaces of the posterior condylar portions, in order to allow the distal portion of the femur to be resected so that the anterior cut and the posterior cut are not parallel, such that the distal extremity of the femur is physically greater in anterior-posterior dimension than portions more proximal, whereby the distal extremity of the femur can be physically captured by the interior surfaces of the femoral component.

According to certain aspects and embodiments of the invention, there is further provided a knee prosthesis which helps impart internal rotation to the tibia as the knee flexes from substantially 0 degrees of flexion to substantially 130 degrees of flexion, such that the tibia is substantially fully internally rotated to an angle of at least approximately 8 degrees in order to allow such flexion to occur in more physiological fashion, to reduce the possibility that the quadriceps will pull the patella undesirably relative to the knee in a lateral direction (lateral subluxation), to allow the patella or its replacement to track the trochlear groove, or any combinations of these.

According to certain aspects and embodiments of the invention, there is further provided a knee prosthesis which helps impart internal rotation of the tibia as the knee flexes between substantially zero degrees and substantially 130 degrees, to at least substantially 8 degrees of internal rotation of the tibia relative to the femur at flexion angles greater than 130 degrees.

According to certain aspects and embodiments of the invention, there is further provided a knee prosthesis which imparts internal rotation of the tibia relative to the femur as the knee flexes from substantially 0 degrees to substantially 130 degrees of flexion, so that the tibia is substantially fully internally rotated relative to the femur to an angle of at least substantially 8 degrees at a flexion angle of substantially 130 degrees, such flexion and internal rotation of the tibia being facilitated at least in part by a twisting moment created by contact of the condyles of the femoral component on the insert.

According to certain aspects and embodiments of the invention, there is further provided a knee prosthesis which imparts internal rotation of the tibia relative to the femur as the knee flexes from substantially 0 degrees to substantially 130 degrees of flexion, so that the tibia is substantially fully internally rotated relative to the femur to an angle of at least substantially 8 degrees at a flexion angle of substantially 130 degrees, such flexion and internal rotation of the tibia being facilitated at least in part by a twisting moment created by contact between the post or other raised portion of the insert and at least one cam of the femoral component.

According to certain aspects and embodiments of the invention, there is further provided a knee prosthesis whose structure facilitates the screw home mechanism.

According to certain aspects and embodiments of the invention, there is further provided a knee prosthesis which allows flexion at flexion angles greater than 130 degrees while allowing internal rotation of the tibia relative to the femur as the knee flexes from substantially 0 degrees to substantially 130 degrees, without the need for a mobile bearing design or to allow the insert to swivel or rotate relative to the tibial component.

According to certain aspects and embodiments of the invention, there are provided methods of designing knee prosthetic components using simulation of a femoral, patella and insert structure, physiological data regarding structure and function of natural knees, and applying at least six force vectors to the structure throughout a desired range of motion to effectively and efficiently simulate forces applied to the tibia in the body: force applied by the patella ligament, ground reaction force, relative force applied by the lateral condyle on the insert, relative force applied by the medial condyle on the insert, force applied by the hamstring muscles, and relative force applied by the cam surfaces of the femoral component on the post or other raised portion of the insert.

According to certain aspects and embodiments of the invention, there are provided methods of designing knee prosthetic components using simulation of a femoral and insert structure and applying to the structure throughout a desired range of motion, force vectors that represent relatively greater forces applied by some ligaments, tendons and muscles than others, such as the relatively great forces applied by the quadriceps when they actuate and by the hamstrings when they actuate.

According to certain aspects and embodiments of the invention, there are provided methods of designing knee prosthetic components using simulation of a femoral and insert structure and applying to the structure a desired set of forces, evaluating the performance of the structure, modifying the structure as simulated in the computer, and repeating the process until a desired design is reached.

According to additional aspects and embodiments of the invention, there is provided a knee prosthesis comprising: a femoral component adapted to fit on a distal end of a femur, the femoral component including a lateral condylar structure and a medial condylar structure, the geometry of the lateral condylar structure being different from the geometry of the medial condylar structure; and an accommodation structure including a lateral proximal surface adapted to cooperate with the lateral condylar structure of the femoral component, and a medial proximal surface adapted to cooperate with the medial condylar structure of the femoral component, the geometry of the lateral proximal surface and the medial proximal surface being different from each other, to assist in imparting internal rotation on the tibia relative to the femoral component as the knee flexes from substantially zero degrees of flexion to substantially 130 degrees of flexion.

According to additional aspects and embodiments of the invention, there is provided a knee prosthesis comprising a femoral component adapted to fit on a distal end of a femur, the femoral component including: an anterior portion which includes an interior surface adapted to interface with the femur; a lateral condylar structure which includes a posterior section which in turn includes an interior surface adapted to interface with the femur; and a medial condylar structure which includes a posterior section which in turn includes an interior surface adapted to interface with the femur; wherein the interior surfaces are adapted to physically capture at least a portion of the femur in the femoral component relative to a distal translation substantially parallel to the anatomic axis of the femur; and wherein all interior surfaces of the femoral component are adapted to allow the femoral component to clear resected portions of the femur physically as the femoral component is rotated onto the femur about its posterior portions during installation.

Certain embodiments and aspects of the invention also provide other characteristics and benefits, and other objects, features and advantages of various embodiments and aspects of the invention will be apparent in the other parts of this document.

DETAILED DESCRIPTION

Figure 1A:
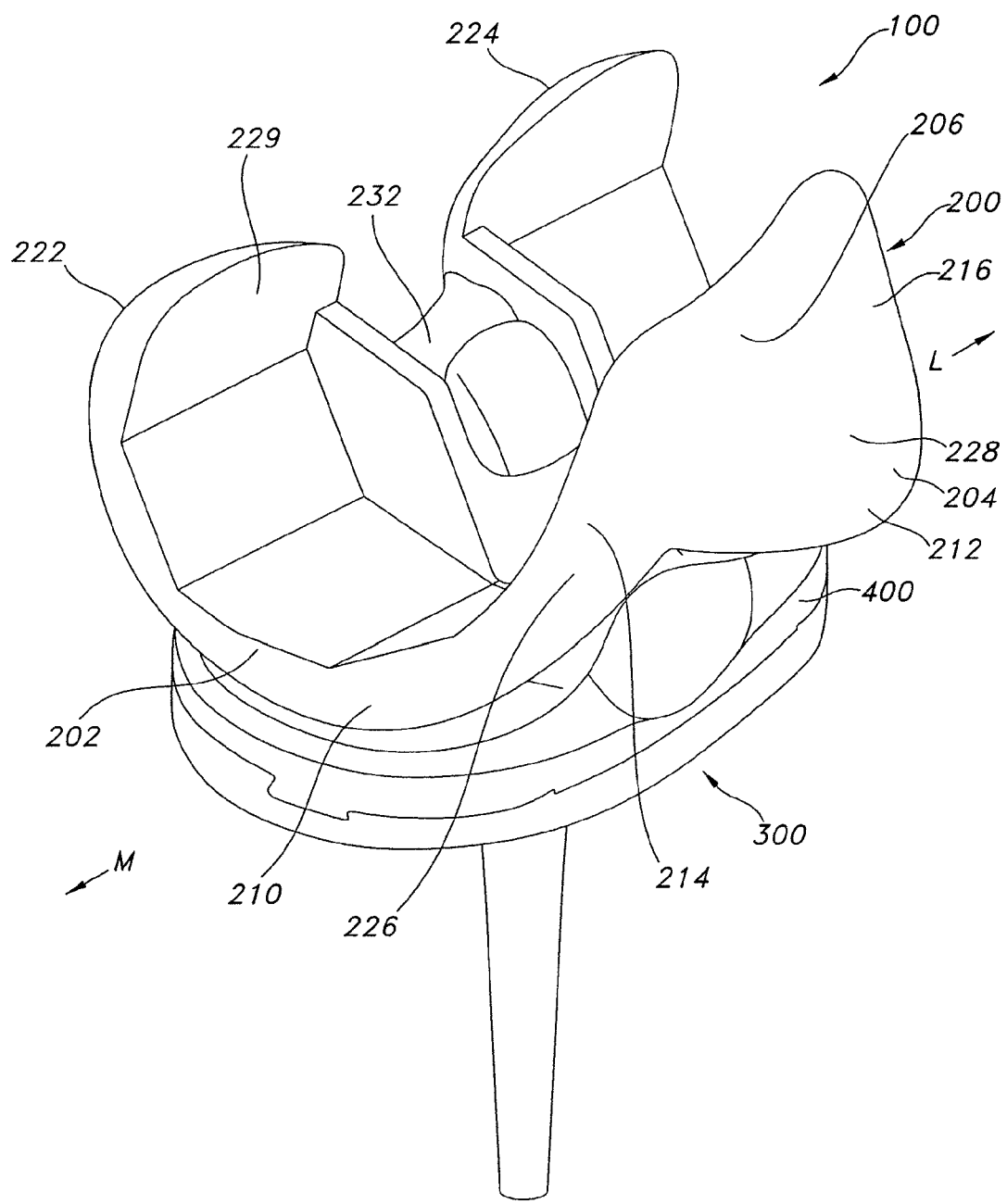
FIG. 1A shows a perspective view of a left knee prosthesis according to an embodiment of the invention.
Figure 1B:
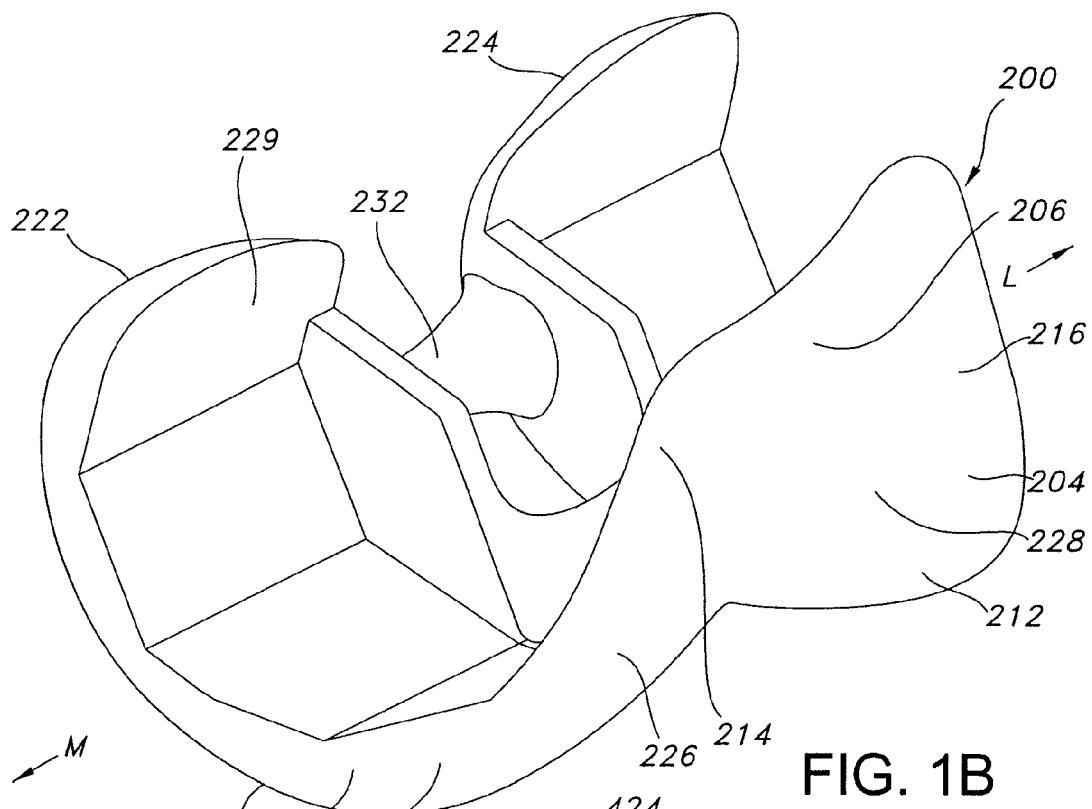
FIGS. 1B-1C show an exploded front perspective view of a femoral component and an insert of a left knee prosthesis according to an embodiment of the invention.

Various embodiments of the invention provide improved knee prostheses for replacing at least a portion of a knee joint between the distal end of a femur and the proximal end of a tibia.

While not wishing to be bound by any particular theory, the inventors have discovered that knee prostheses which more faithfully and closely replicated the function, anatomy and physiology of the normal human knee would yield a number of advantages. Among other things, such prostheses would provide an increased range of motion and would function more normally particularly in extension, deep flexion and during normal gait. They would take into account the forces imposed on the knee by quadriceps and hamstrings actuation, forces which great in magnitude but not fully considered in conventional knee prosthesis design. Knee prostheses according to various aspects of the invention recognize that during movement of the knee, particularly during flexion, the position and orientation (kinematics) of the bones of the knee are a result of achieving equilibrium of the forces that cause motion of the knee (kinetics). Additionally, the shape of the articular surfaces (anatomy) acting in combination with forces imposed by various muscles, ligaments and tendons, determines the direction of the large contact forces. Therefore, aspects of the invention take into account that anatomy influences kinetics and kinetics determine kinematics.

Conventional knee prostheses have been developed without recognition of the full range of kinetics of active knee movement. Many are primarily concerned with achieving greater flexion. However, in addition to flexion and extension, motion of the knee is both rotational and translational. The femoral condyles both roll and glide as they articulate with respect to the tibial plateaus. As the knee moves from full extension into flexion the axis of rotation between the femur and the tibia moves posteriorly relative to both the femur and the tibia. Additionally, in the normal human knee, internal rotation of the tibia relative to the femur occurs as the knee flexes between full extension and approximately 130° of flexion. Knee prostheses according to various aspects of the invention provide various surfaces on at least the femoral component and the insert which promote such greater flexion, the screw home mechanism, internal rotation of the tibia relative to the femur as the knee flexes, and other characteristics of the natural knee.

According to some aspects of the invention, the design of knee prosthesis components is conducted using a process which (1) tests various performance aspects of a proposed design using computer simulation of the design and various forces imposed upon it, (2) allows analysis of the test results for development of improvements to the proposed design; (3) uses test results to change the proposed design (either manually or automatically), (4) tests various performance aspects of the modified design using computer simulation of the design and various forces imposed upon it, and (5) repeats these tasks in an iterative fashion until the performance testing shows an iteratively modified design to feature acceptable performance characteristics. It is also significant that in such performance testing, the performance of the proposed design is tested using forces that occur at various points in various activities, so that the performance testing is dynamic across extended ranges of motion and takes into account considerable forces placed on the design by actuation of the quadriceps and hamstring muscles, for example, and the consequent kinetic and kinematic effects of such forces.

A preferred embodiment of a knee prosthesis according to the invention is shown in FIGS. 1A-1C and 2-4, and identified by the numeral 100. The knee prosthesis 100 shown in these figures is designed to replace at least a portion of a left knee joint between the distal end of a femur and the proximal end of a tibia. A mirror image (not shown) of knee prosthesis 100 will replace at least a portion of a right knee between the distal end of a femur and the proximal end of a tibia.

The knee prosthesis 100 includes a femoral component 200 for mounting to a distal end of a femur, a tibial component 300 for mounting to a proximal end of a tibia, and an insert 400.

Embodiments of the femoral component 200 preferably include a medial condylar section 202, a lateral condylar section 204 and a trochlear groove 206 joining the anterior portions 214, 216 of the medial and lateral condylar sections 202, 204 together. The medial and lateral condylar sections 202, 204 are disposed apart from one another to form an intercondylar recess or notch 208. Each condylar section 202, 204 has an outer surface 210, 212 for engaging a tibial component 300 or insert 400 as will become apparent. The outer surfaces 210, 212 of each condylar section 202, 204 preferably have distal portion 218, 220 for engaging a portion of the tibial component 300 or insert 400 when the knee joint is extended and partially flexed, and posterior portions 222, 224 for engaging a portion of the tibial component 300 or insert 400 when the knee joint is flexed at angles of substantially 90° or greater.

Figure 20:
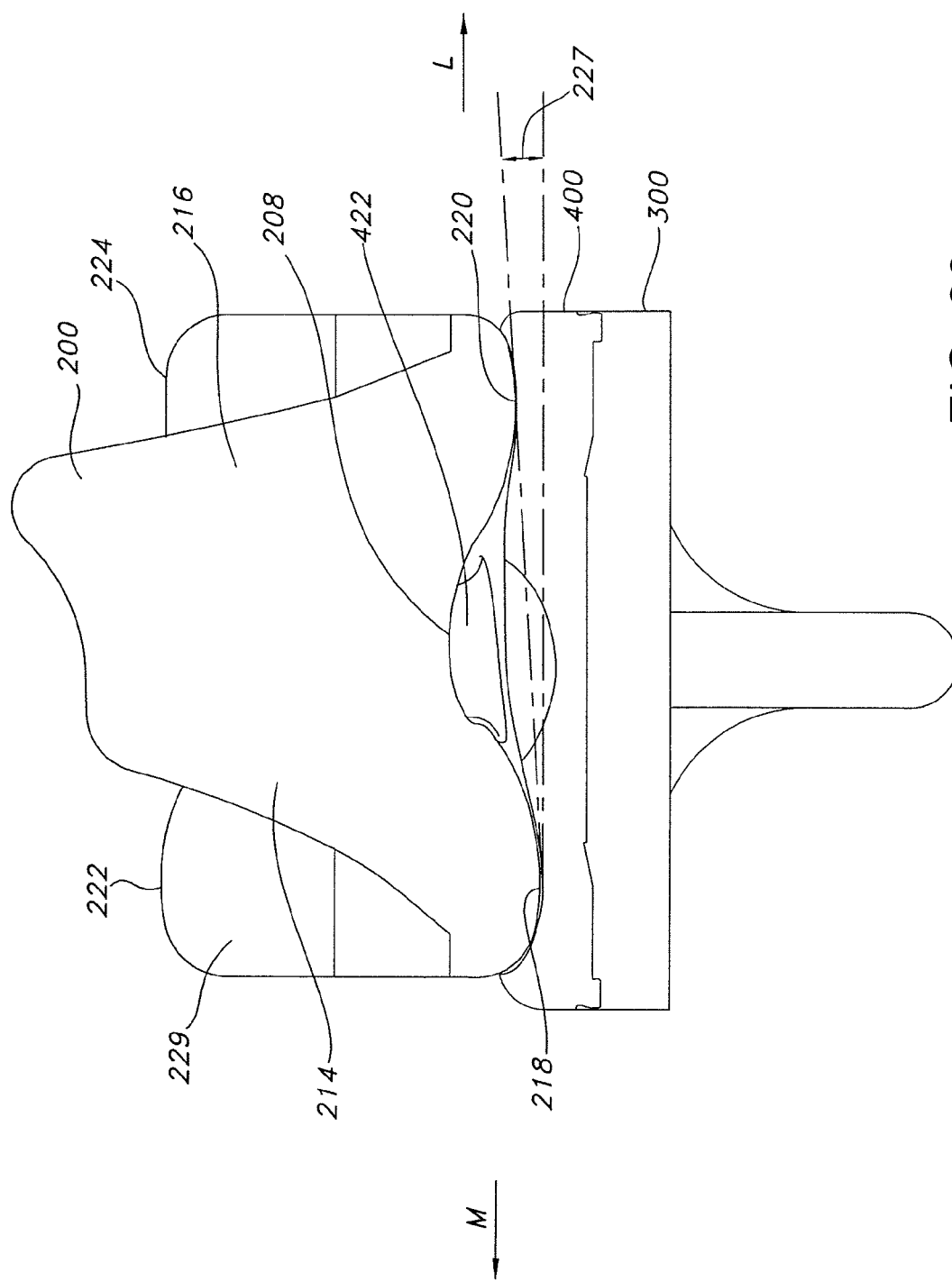
FIG. 20 shows a front plan view of a left knee prosthesis according to an embodiment of the invention.

Embodiments of a femoral component 200 according certain aspects of this particular nonlimiting embodiment of the invention also replicate the physiological joint line 227 of a normal knee as shown in FIG. 20. The physiological joint line 227 may be considered to be a line extending between the distal most portions of each condyle at a knee flexion angle of zero degrees. This physiological joint line is oriented at an angle of approximately 93 degrees from the mechanical axis of the leg (which could also be considered to be 87 degrees from the mechanical axis of the leg depending on perspective), or approximately 3 degrees from horizontal as shown in FIG. 20. The joint line established by prostheses according to certain embodiments and aspects of the invention preferably replicate this physiological joint line 227 as shown in that drawing.

Embodiments of the femoral component 200 preferably have a thickness approximately matching the bone resection necessary for the total knee replacement.

Figure 1:
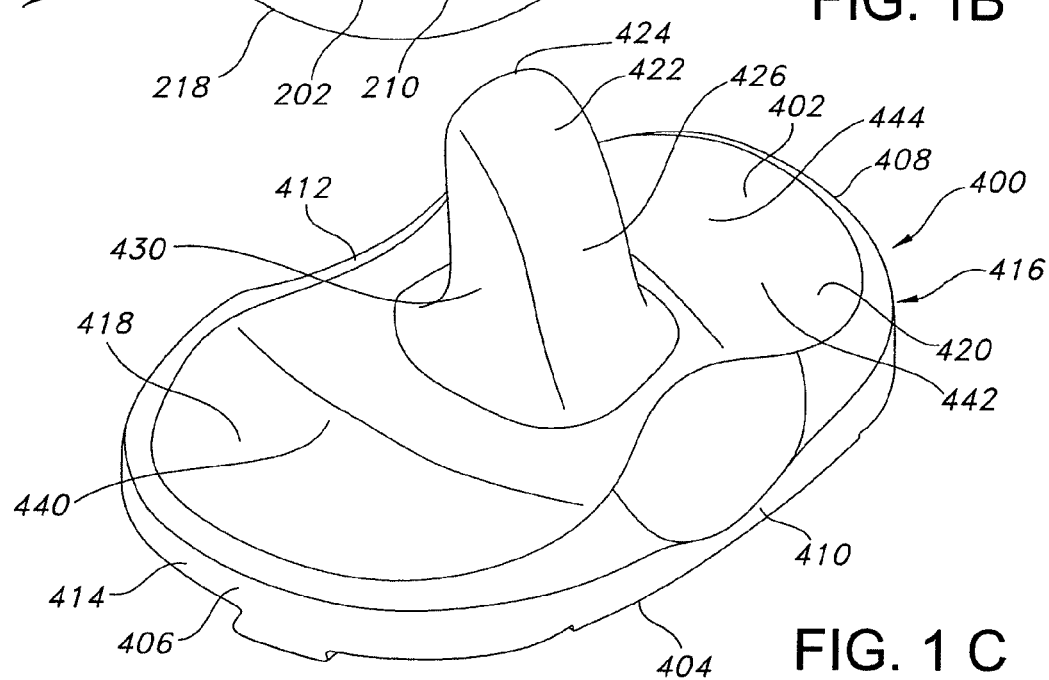
Figure 2:
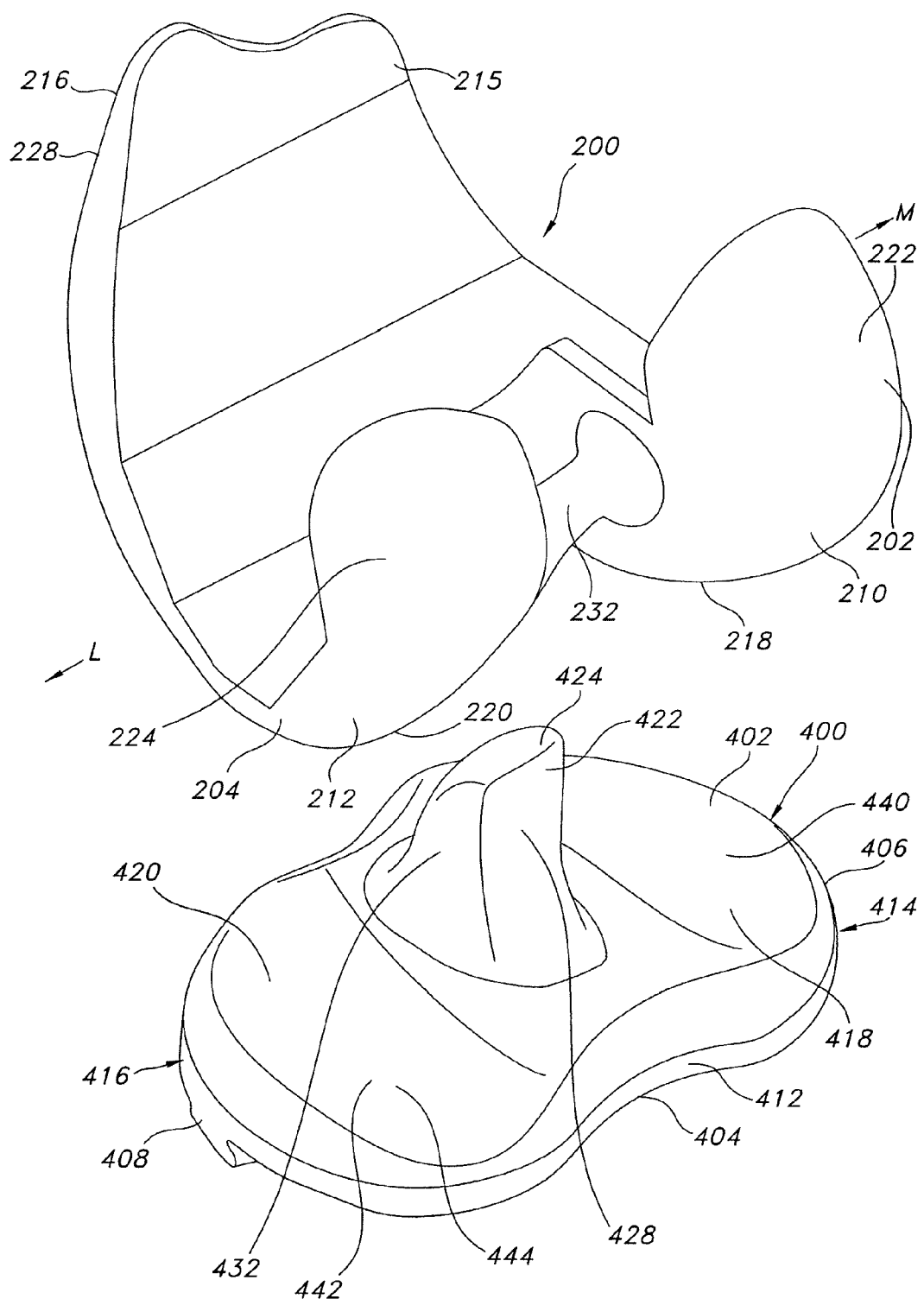
FIG. 2 shows an exploded back perspective view of a femoral component and an insert of a left knee prosthesis according to an embodiment of the invention.
Figure 3:
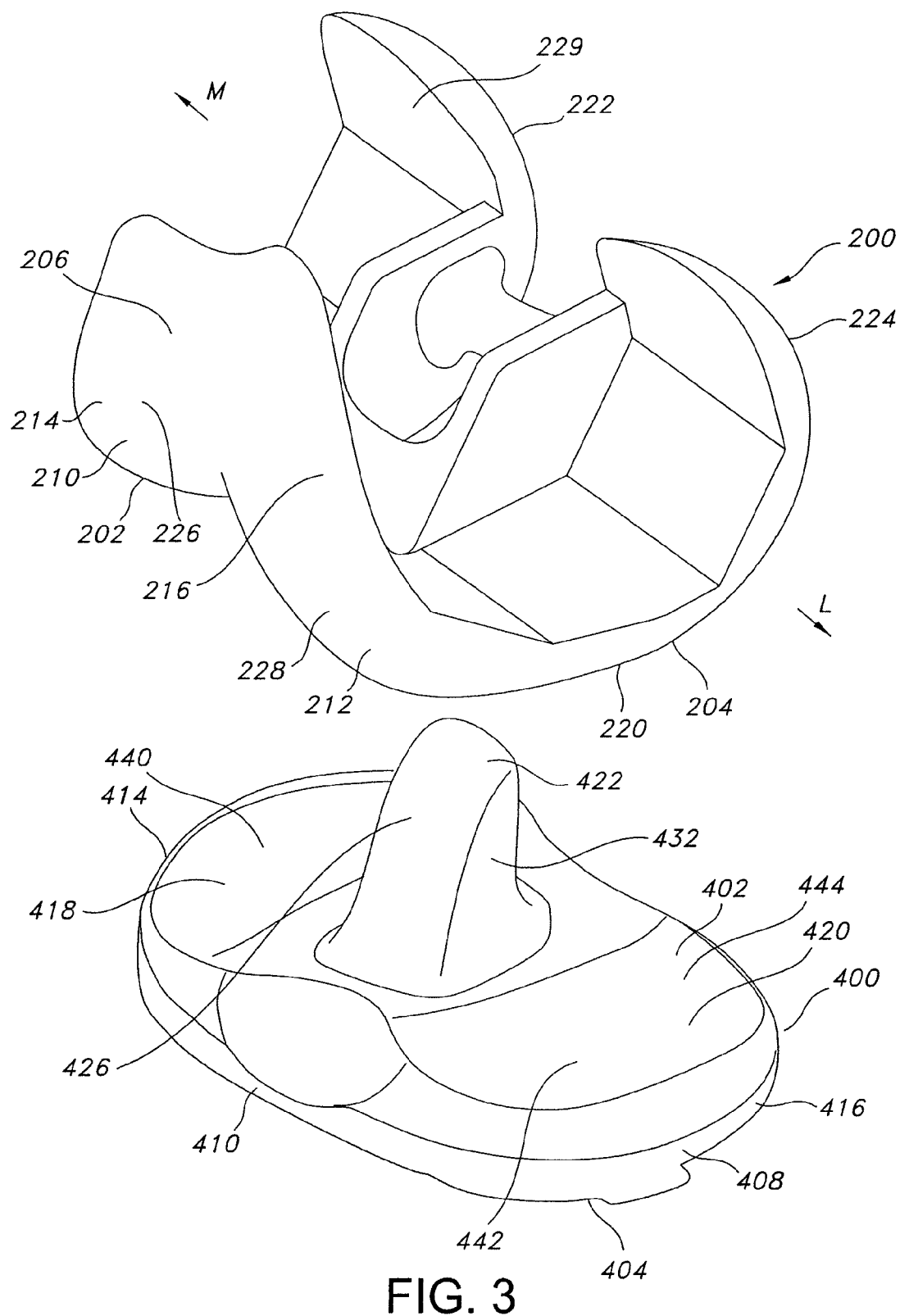
FIG. 3 shows an exploded front perspective view of a femoral component and an insert of a left knee prosthesis according to an embodiment of the invention.

Embodiments of the femoral component 200 also preferably have a lateral condylar section 204 that is different in geometry than the geometry of the medial condylar section 202. In the embodiment shown in FIG. 1, the size of lateral condylar section 204 is smaller than the size of medial condylar section 202 so that its outer surface distal portion 220 does not extend as far distally as does the outer surface distal portion 218 of medial condylar section 202.

The femoral component 200 may include a rounded medial profile. According to certain embodiments, for example, it may feature a medial profile which includes a single radius from 15-160°, and may also include a lateral profile that is less round or curved distally, with a single radius from 10-160°.

In the normal human knee, the patella glides caudally on the femoral condyles from full extension to full flexion. By 20 to 30° of flexion, the patella first begins to articulate with the trochlear groove. At extreme flexion, the patella lies in the intercondylar recess. Initially the patella contact occurs distally and with increased flexion the contact areas shift proximally on the patella. Patellofemoral contact force is substantially body weight when walking, and increases to substantially 5 times body weight when stair climbing. These contact forces therefore impose a substantial load on the knee joint, which prostheses according to certain embodiments and aspects specifically take into account.

Knee prostheses according to certain embodiments and aspects of the invention incorporate features that allow the patellar implant of the knee prostheses to move in a way similar to the normal human knee and to withstand the normal patellofemoral contact force without unnecessary ligament release. These features include various aspects of the shape of portions of the medial condylar section 202 and the lateral condylar section 204, to be more consistent with natural anatomical geometry. For instance, anterior portion 216 of lateral condylar section 204 can be configured to extend further anteriorly than anterior portion 214 of medial condylar section 202, or to be more abruptly shaped on its surface that cooperates with the patella, so that it acts as a buttress to guide the patella at low flexion angles and in extension.

Femoral components according to certain embodiments and aspects of the invention can also include a patella-friendly trochlear groove 206. The trochlear groove 206 in such embodiments is substantially S-shaped and lateralizes the patella 500. The trochlear groove 206 further allows for a smooth transition between the anterior portions 214, 216 of the condylar sections and intercondylar notch 208. This further reduces the contact forces on the patella 500.

Figure 21:
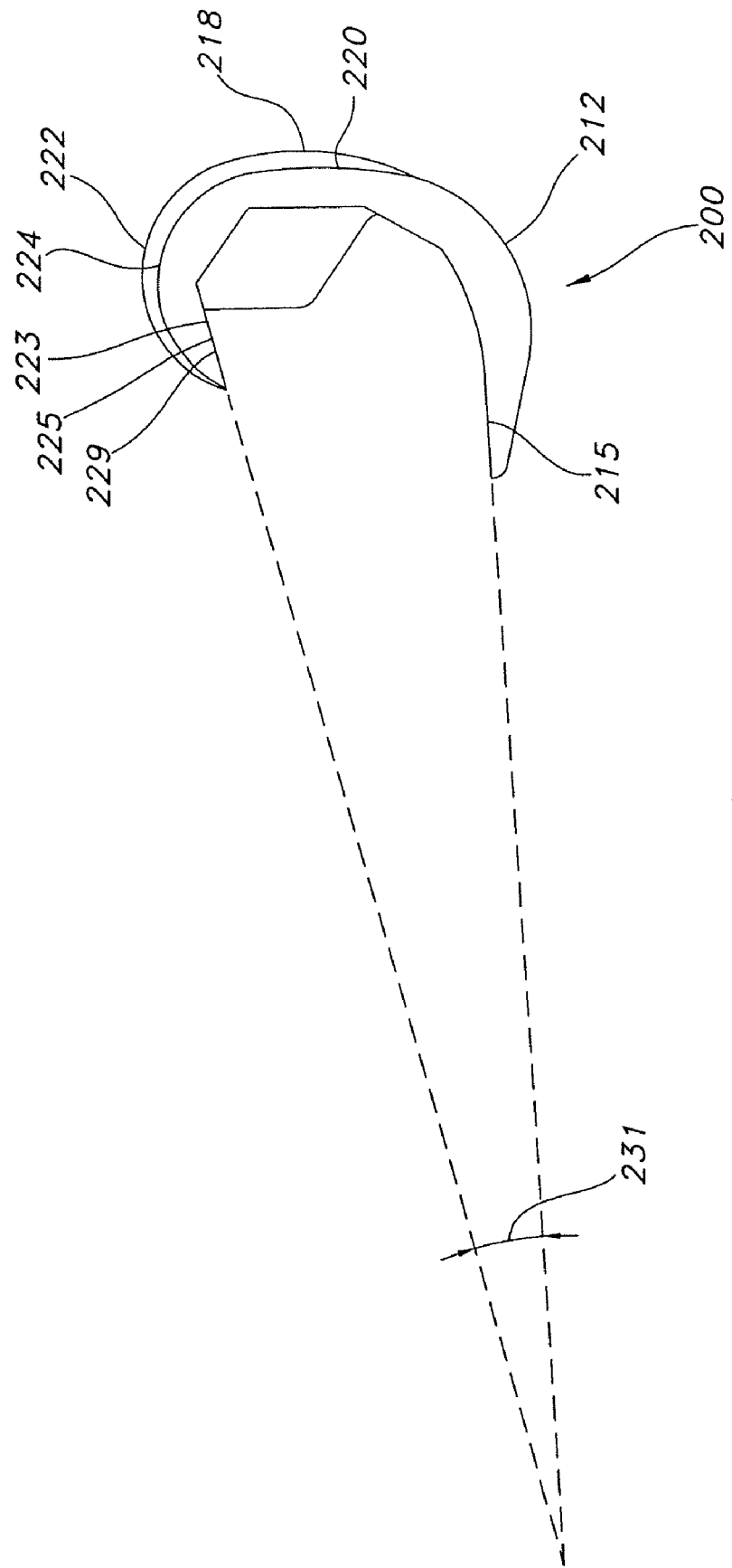
FIG. 21 shows certain aspects of a femoral component of a knee prosthesis according to an embodiment of the invention.

Femoral components 200 according to certain embodiments and aspects of the invention can include flexed or backdrafted substantially planar interior or bone interface surfaces 223 and 225 (collectively, backdrafted surface 229), on the anterior surfaces of posterior portions of medial condyle section 222 and lateral condyle section 224. Preferably, the interior surfaces 223, 225 are coplanar and are oriented so that their planes converge with a plane formed by the interior surface 215 on the posterior side of anterior portions 214 and 216 of the femoral component 200 as shown more clearly in FIG. 21. In this way, proximal portions of these posterior condylar interior surfaces 223 and 225 are located closer to the plane of the interior surface 215 of the anterior portion of the femoral component 200 than are distal portions of surfaces 223 and 225. Preferably, the convergence angle is in a range of between 1 and 30 degrees, and more preferably, the convergence angle is approximately 15 degrees. The backdrafted surface 229 extends the articular surface of the femoral component 200 with minimal bone resection. Removing less bone decreases the likelihood of later femoral fracture. It also minimizes the likelihood that the femoral component 200 will be forced off the end of the femur in deep flexion, since it serves to lock onto or capture the distal end of the femur in the femoral component 200.

The femoral component 200 with the backdrafted surface 229 can be installed by hinging and rotating the femoral component 200 onto the resected femur about the posterior portions of the condyles of the femur. The inventors have discovered that it is possible, by configuring all anterior surfaces of the femoral component 200 correctly, as shown in FIGS. 4-11 and 21, for example, to allow those surfaces to physically clear the resected bone as the femoral component is rotated onto the femur during installation. Among other ways to accomplish this configuration are: (1) to cause the interior surfaces to create a shallow interior space; and/or (2) to adjust angles and/or dimensions of the chamfered surfaces that connect the interior surfaces 223, 225 of condylar sections 202 and 204 and/or interior surface 215 of the anterior portion of the component 200 to the bottom interior surface of the component 200.

Interior surfaces of the component 200, including surfaces 215, 223 and 225, need not be planar or substantially planar to accomplish the objective of capturing or locking onto the femur. For instance, one or more of them may be curved or partially curved and accomplish this objective by orienting one or both of the interior surfaces of the condylar sections 202, 204 relative to the interior surface of the anterior portion of the femoral component at other than parallel.

Certain embodiments of the femoral component 200 may include an anterior cam 230, as shown in FIGS. 4-11. As explained further below, the anterior cam 230 works with the post or other raised portion 422 of the insert 400 to provide anterior stabilization during early gait. The anterior cam 230 preferably includes a large radius to increase the contact area between the anterior cam 230 and the post 422. The anterior cam surface 230 preferably does not engage the anterior surface of the post 422 for approximately 1-2 mm.

Figure 22:
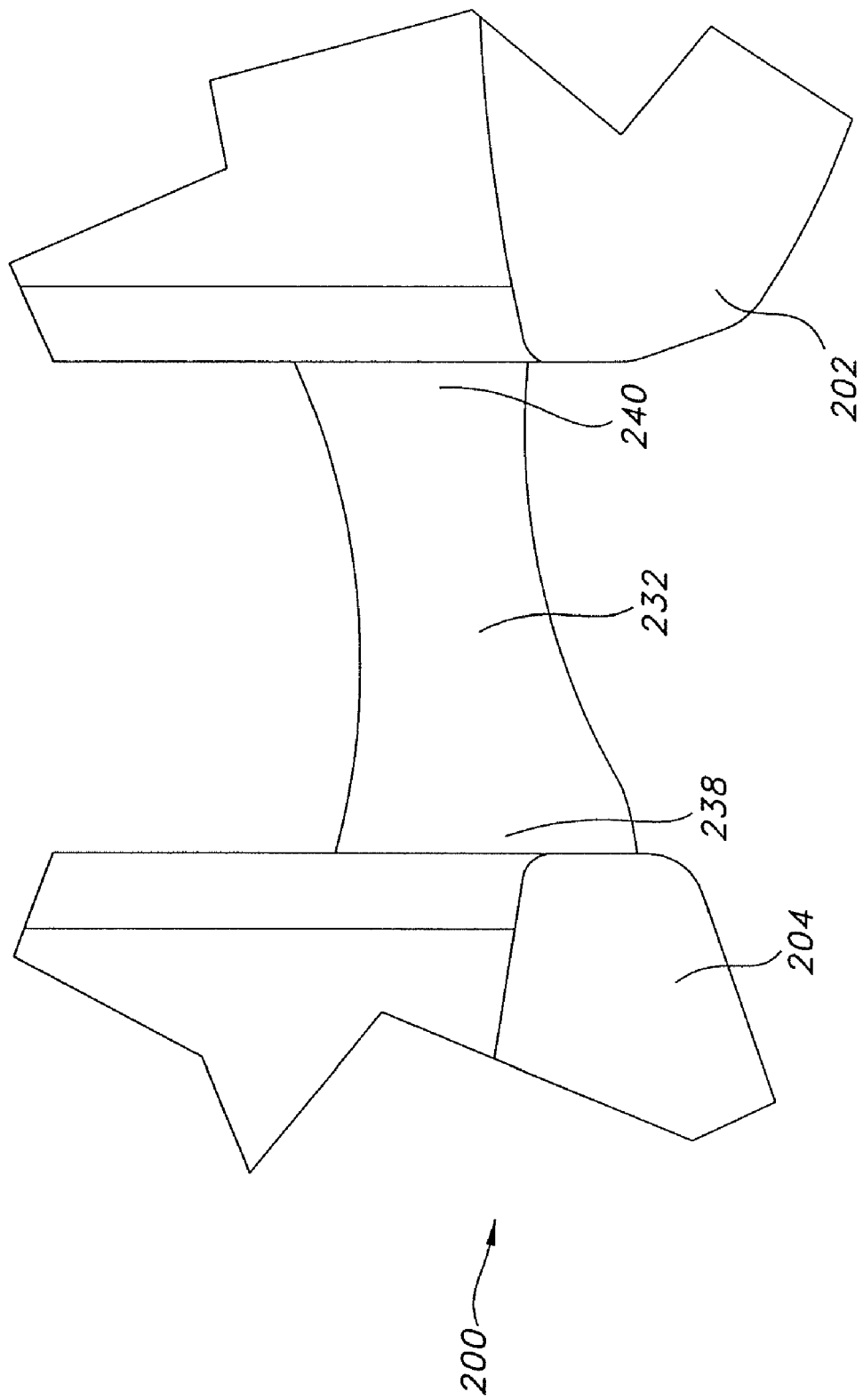
FIG. 22 shows certain aspects of a cam of a femoral component of a knee prosthesis according to an embodiment of the invention.

Certain embodiments of the femoral component 200 may include a posterior cam 232 as shown in FIGS. 4-11, among other places as well as in a closer view in FIG. 22. Preferably, the posterior cam 232 is asymmetrical. The lateral side 238 may be larger than the medial side 240, for example, as shown in FIG. 22. As explained further below, the larger lateral side 238 provides optimal contact between the posterior cam 232 and the post 422 during axial rotation, to assist in imparting internal rotation to the tibia relative to the femur as the knee flexes. In general, the posterior cam 232 engages the post 422 between 50-60° flexion. The post 422 may be thickened distally for additional strength.

Prostheses according to certain embodiments of the invention, which do not need to serve a posterior stabilization function, such as those which can be characterized as cruciate retaining, need not have a post or other raised surface 422 on insert 400, or cams, such as cams 232 or 230. In such embodiments and aspects, other surfaces such as portions of the medial and lateral condylar sections 202, 204 acting without a post or raised surface 422, for example, achieve or help achieve objectives of aspects of the invention, including allowing or imparting internal rotation to the tibia relative to the femur as the knee flexes, such as from substantially 0 degrees to substantially 130 degrees.

Certain embodiments of the femoral component 200 may include conventional attachment aids for helping to secure the femoral component 200 to a distal end of a femur. Such attachment aids may include one or more pegs, fins, surface treatments including bone ingrowth surfaces, surfaces for accommodating spacers, shims or other structures, or as otherwise desired.

Tibial components 300 according to certain embodiments and aspects of the invention include a tray or base member for being secured to a proximal end of a tibia. The base member can include a stabilizing post, which is insertable into the tibial medullary canal and provides for the stabilization of the tibial component 300 on the tibia.

Tibial components according to embodiments and aspects of the invention feature a tray member which includes a proximal or upper surface, a distal or lower surface, a medial surface, a lateral surface, an anterior or front surface, and a posterior or rear surface. The proximal surface may be substantially flat and planar. The tray member preferably includes attachment aids for helping to secure the tray member to a proximal end of a tibia. Such attachment aids may include one or more pegs, fins, screws, surface treatments, etc.

Femoral components 200 and tibial components 300 according to certain embodiments and aspects of the invention may be constructed in various manners and out of various materials. For example, the femoral component 200 and tibial component 300 may be machined, cast, forged or otherwise constructed as a one-piece integral unit out of a medical grade, physiologically acceptable metal such as a cobalt chromium alloy or the like, in various sizes to fit a range of typical patients, or may be custom-designed for a specific patient based on data provided by a surgeon after physical and radiography examination of the specific patient.

Inserts 400 according to certain embodiments and aspects of the invention include a proximal or upper surface 402, a distal or lower surface 404, a medial surface 406, a lateral surface 408, an anterior or front surface 410, and a posterior or rear surface 412. For convenience, such an insert 400 may be considered to feature a medial side 414 and a lateral side 416, corresponding to medial and lateral sides of the limb in which the insert is to be installed.

The proximal surface 402 of the particular insert 400 according to one embodiment of the invention shown in the drawings has a medial portion 418 for engaging the outer surface 210 of the medial condylar section 202 of the femoral component 200, and a lateral portion 420 for engaging the outer surface 212 of the lateral condylar section 204 of the femoral component 200.

Inserts 400 according to certain embodiments and aspects of the invention can include a central post or raised portion 422 as shown in the drawings. The post 422 includes a proximal surface 424, an anterior surface 426, a posterior surface 428 and medial and lateral side surfaces 430, 432. The anterior surface 426 of post 422 in an embodiment of the insert, is tapered or curved at a desired angle with respect to the distal surface 404 of the insert 400 to minimize impingement of the patella or a patellar implant 500 in deep flexion. The base can be tapered as desired in a posterior direction from the anterior surface 426 to minimize impingement of the intercondylar notch 208 of femoral component 200 in hyperextension.

Inserts 400 of certain embodiments and aspects of the invention as shown in the drawings include an anterior curved surface. The anterior curved surface allows room for the patellar tendon (not shown). The insert may also include a posterior curved surface. The result of the posterior curved surface is the removal of material that may impinge on the posterior cortex of the femur in deep flexion. The radius of curvature may vary as desired to provide sufficient room for maximal flexion.

The distal surface of the insert 400 according to certain embodiments and aspects of the invention may be substantially flat or planar for contacting the proximal surface of the tray member of the tibial component 300. The distal surface preferably includes a dovetail or other appropriate locking mechanism that consists of an anterior portion and a posterior portion. However, any conventional method for positioning and/or retaining the insert relative to the tray member, whether constrained or unconstrained, may be used. In other embodiments, the insert 400 may be allowed to articulate relative to the tray of the tibial component 300.

On the proximal surface 402 of inserts 400 according to certain embodiments and aspects of the invention, parts of the medial portion 418 of the proximal surface and parts of the lateral portion 420 are shaped to cooperate with outer surfaces 210 of the medial condylar section of femoral component 200 and outer surfaces 212 of the lateral condylar section of the femoral component, as the knee flexes and extends. These parts are referred to as medial insert bearing surface 440 and lateral insert bearing surface 442.

Figure 23:
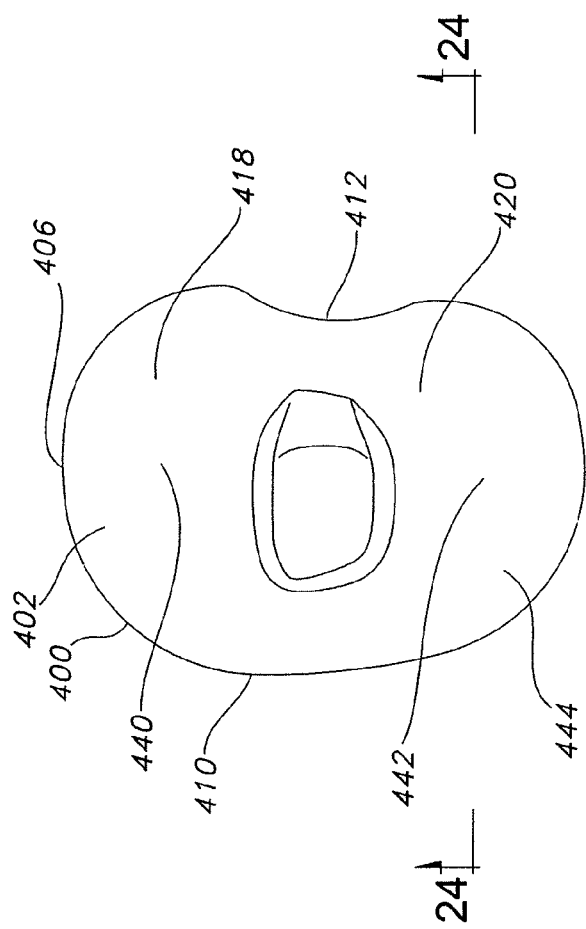
FIG. 23 shows certain aspects of a proximal surface of an insert of a knee prosthesis according to an embodiment of the invention.
Figure 24:
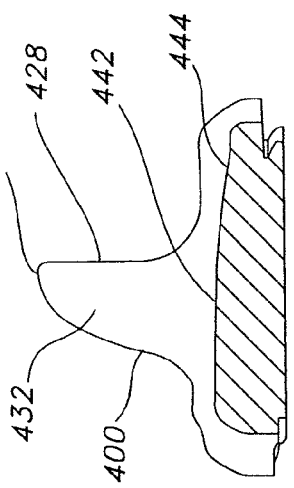
FIG. 24 is a cross sectional view showing certain aspects of a lateral bearing surface of a knee prosthesis according to an embodiment of the invention.

From a sagittal aspect, as shown in FIGS. 4-11 and also in FIGS. 23 and 24, posterior parts of the lateral bearing surface 442 of the particular insert shown in the drawings features a reverse slope; that is, the lateral bearing surface slopes toward the bottom or distal surface of the insert 400 as the lateral bearing surface progresses toward the posterior or back periphery of the insert 400, preferably either through a convex arc or a straight slope. The purpose of the slope is to change the direction of the contact force between the lateral bearing surface 442 and the lateral condylar section 204, in order to add an anterior force on the lateral bearing surface 442 greater than a corresponding anterior force on the medial bearing surface 440 at some angles of knee flexion, to produce or help produce a twisting moment about the longitudinal axis of the tibia or impart or assist in imparting internal rotation of the tibia as the knee flexes. Preferably, this rotation-imparting surface 444 is configured to impart or assist inward tibial rotation relative to the femur as the knee flexes between substantially 0 degrees of flexion to substantially 130 degrees of flexion, the internal rotation angle achieving a magnitude of at least substantially 8 degrees at substantially 130 degrees of knee flexion. Since the contact force vector is perpendicular to the lateral bearing surface 442, during rollback in the lateral compartment, a component of the contact force vector is generally parallel to the generally anteriorly oriented contact vector acting on the post 422. Accordingly, this contact force not only can help delay engagement of the post 422 with the posterior cam 232, but it can also beneficially reduce the force required by the post 422 to produce lateral rollback, resist anterior motion of the femoral component 200 relative to the insert 400, and resist total force which is absorbed by the post 422 in accomplishing posterior stabilization of the knee.

It is also possible to generate the tibial inward rotation inducing couple on the insert 400 by the femoral component 200 not only by using the posterior cam 232 as discussed below, but also by altering the shape of parts of the medial insert bearing surface 440 or using other structures, surface shaping or other techniques, or any combination of them, as desired.

Preferably, the lateral insert bearing surface 442 of the insert as shown in the drawings features a curved generally concave portion which sweeps laterally from its anterior extremity to approximately its middle, and then back medially from its middle to its posterior extremity, as shown in FIG. 23, for example. Such a swept surface helps guide the lateral condylar section 202 as the locus of its contact points with the insert 400 move in a posterior direction as the knee flexes.

Inserts 400 according to certain embodiments and aspects of the invention may be constructed in various manners and from various materials. For example, they may be machined, molded or otherwise constructed as a one-piece, integral unit out of medical grade, physiologically acceptable plastic such as ultra high molecular weight polyethylene or the like, in various sizes to fit a range of typical patients, or may be custom-designed for a specific patient based on data provided by a surgeon after physical and radiographic examination of the specific patient. The material can be treated, for example, by radiation, chemistry, or other technology to alter its wear properties and/or strength or hardness. Portions of various surfaces of inserts 400 can be treated with radiation, chemicals or other substances or techniques to enhance wear resistance properties; they can also be subjected to suitable surface treatments for such purposes and others.

If the medial condylar section 202 and the lateral condylar section 204 of the femoral component 200 were the same size, the insert 400 shown in the drawings would be thinner between its lateral insert bearing surface 442 and its distal surface 404 than between its medial insert bearing surface 440 and that distal surface 404. Such thinness may become unacceptable in regions between the rotation inducing surface 444 and the distal surface 404 in the posteriolateral region of the insert 400. To compensate, lateral parts of the insert 400 may be created thicker than medial parts, as shown for example in FIG. 20, so that the lateral insert bearing surface 442 is "higher" or more proximal than the medial insert bearing surface 440. In certain embodiments of the insert 400 as shown for example in FIG. 20, a line drawn between the most distal part of the medial insert bearing surface 440 and the most distal part of the lateral insert bearing surface 442 and denominated physiological joint line 227, forms an approximately 3 degree angle from a line perpendicular to the mechanical axis of the leg or in many insert 400 structures, substantially 3 degrees from the plane of the distal surface of the insert 400. This 3 degree angle is similar to the structure of the human knee, where the physiological joint line is usually substantially 3 degrees from the mechanical axis of the joint. The lateral contact point 436 of the femoral component 200 and the insert 400 is initially higher than the medial contact point 434. During flexion, as the lateral condyle 204 rolls posteriorly, the lateral femoral condyle 204 moves down the arc or slope of tibial rotation inducing surface 444 of insert 400.

In some cases, the epicondylar axis 242 (the line connecting the lateral epicondylar prominence and the medial sulcus of the medial epicondyle) could have a tendency to decline, which could cause rotation about the long axis of the femur and might cause laxity of the LCL. According to certain embodiments of the invention, it would be possible to keep the epicondylar axis 242 at the same height, by causing the sagittal curve of the posterior portion 224 of the lateral condyle 204 to be extended outwardly as could be visualized with reference to, for instance, FIGS. 4-11. For example, at 155° flexion, the lateral contact point 434 could decline approximately 2.6 mm, so that 2.6 mm would be added to the lateral condyle 204 thickness at a point corresponding to 155° flexion on the condyle to accomplish such a result, although other structures could be created to achieve the same end.

When assembled, the femoral component 200 shown in the drawings is positioned on the insert 400 so that there is a slight posterior overhang. This optimizes the anterior-posterior patella ligament force components. The overhang may be much less than in conventional knee prostheses. For example, in conventional knee prostheses, the posterior overhang of the femoral component 200 may be as much as 6 mm. However, in knee prosthesis according to certain embodiments and aspects of the invention, the posterior overhang of the femoral component 200 is approximately 2 mm.

As explained above, axial rotation is normal in knee joint motion. The "screw-home" mechanism is example of this motion. In the normal knee, during knee extension, the femur is positioned anteriorly on the tibial plateau. During the last 20° of knee extension, the femur glides anteriorly on the tibia and produces external tibial rotation. This screw-home mechanism in terminal extension results in tightening of both cruciate ligaments and locks the knee such that the tibia is in the position of maximal stability with respect to the femur.

When the normal knee begins to flex, posterior glide of the femur begins first on the lateral tibial surface. Between approximately 0° and 130° of flexion, posterior glide on the lateral side produces relative tibial internal rotation, a reversal of the screw-home mechanism.

Knee prostheses 100 according to certain embodiments of the invention incorporate an allowance that mimics the screw-home mechanism. The screw-home allowance may be achieved by incorporating a swept surface on the lateral surface 416 of the insert 400. The screw-home allowance is illustrated most clearly in FIG. 12. FIGS. 12-19 demonstrate that as the knee flexes from approximately zero degrees to approximately 130 degrees, the femoral component 200 and the insert 400 rotate relative to each other generally about a closely grouped set of medial contact points 436. As the knee flexes, the femoral component 200 rotates externally relative to the insert 400, which would be fixed on a tibial component 300 in a fully assembled knee prosthesis 100; or considered from the other perspective, the insert 400 and the tibia rotate internally relative to the femoral component 200 and the femur. The asymmetrical shape of the posterior cam 232 reduces force on the central post 422 that would oppose this rotation.

Figure 4:
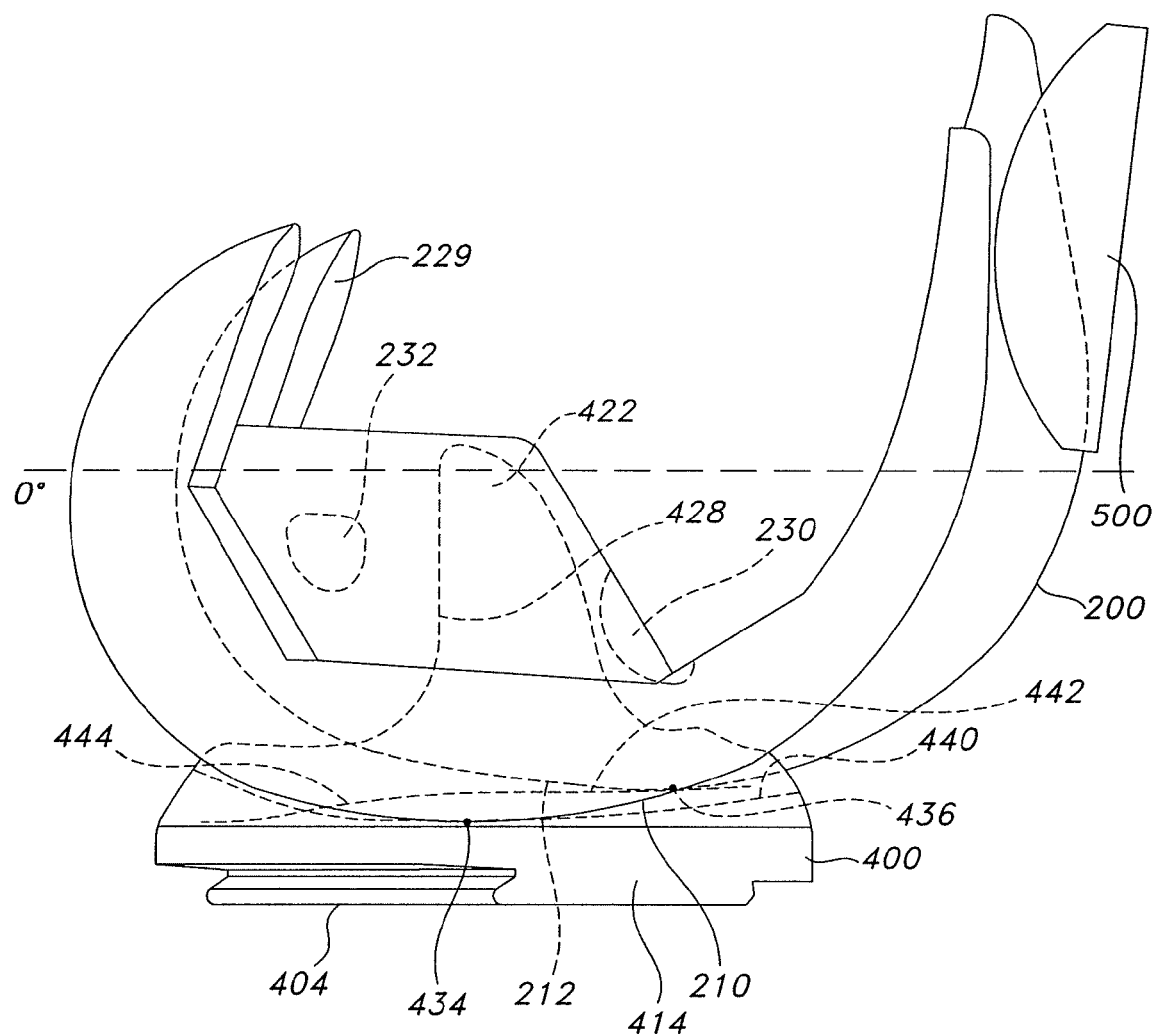
FIG. 4 is a side view of portions of a left knee prosthesis according to an embodiment of the invention showing the kinematics of the left knee at full extension.
Figure 5:
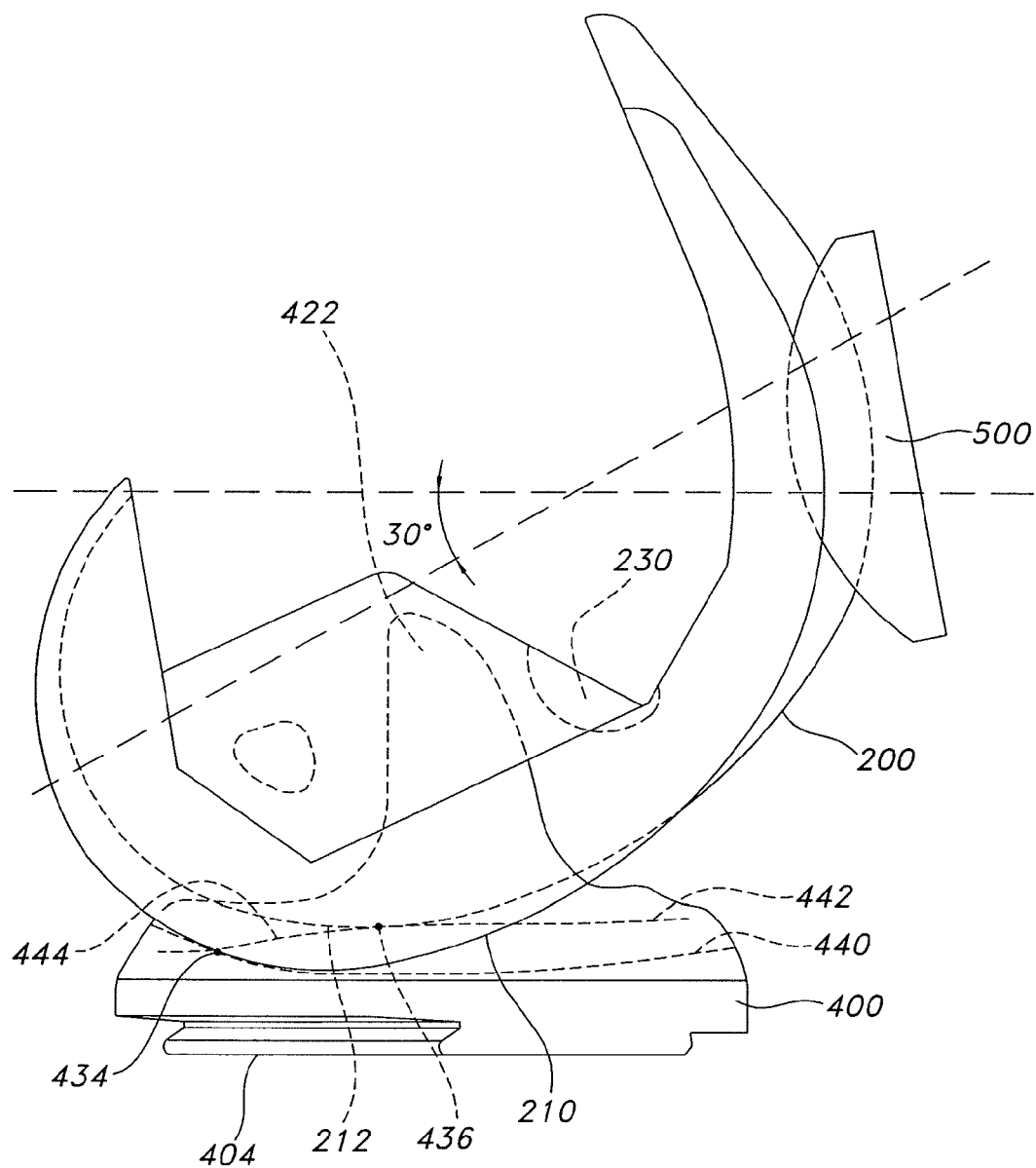
FIG. 5 is a side view of portions of a left knee prosthesis according to an embodiment of the invention showing the kinematics of the knee at 30° flexion.
Figure 9:
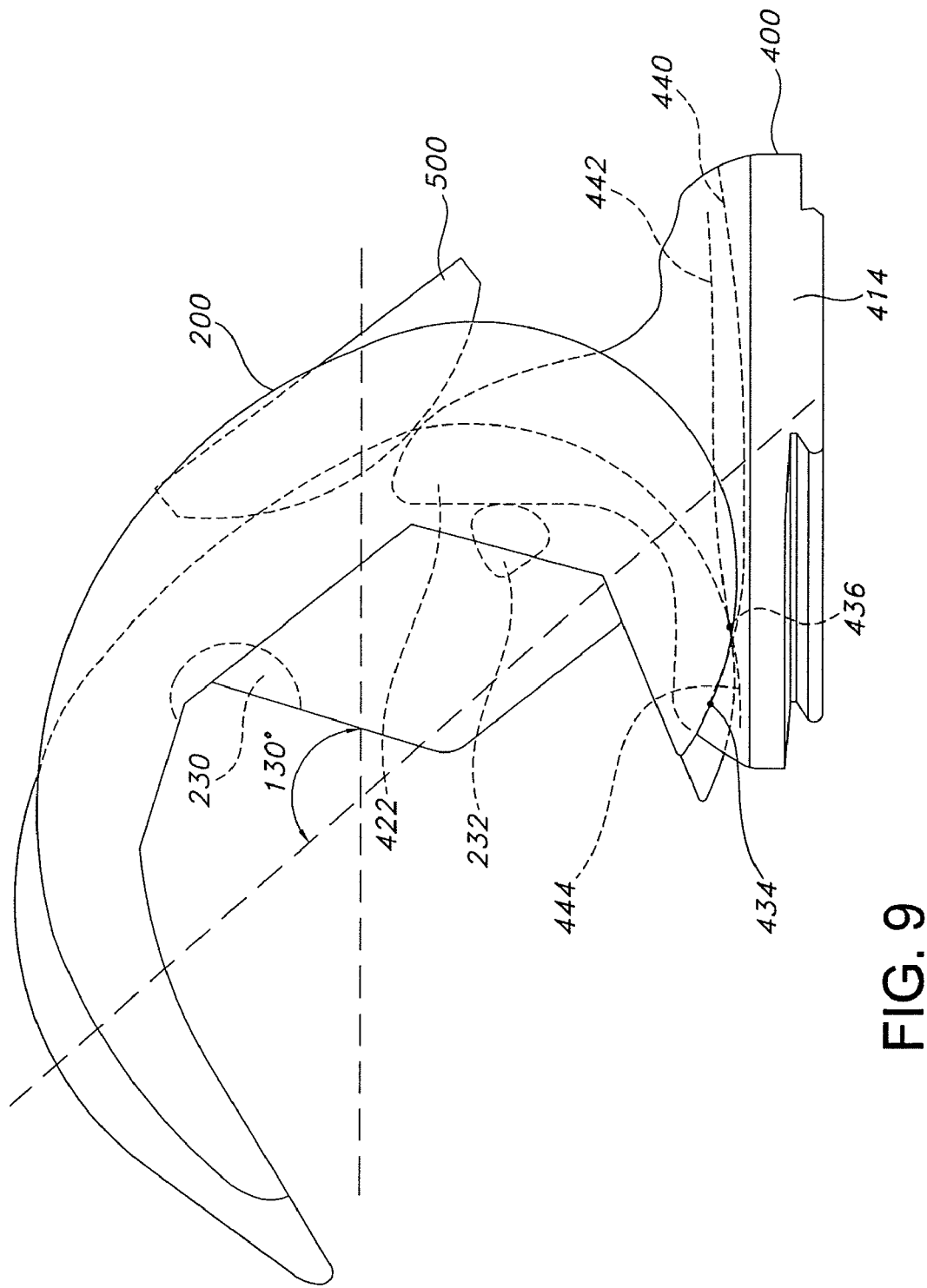
FIG. 9 is a side view of portions of a left knee prosthesis according to an embodiment of the invention showing the kinematics of the knee at 130° flexion.
Figure 10:
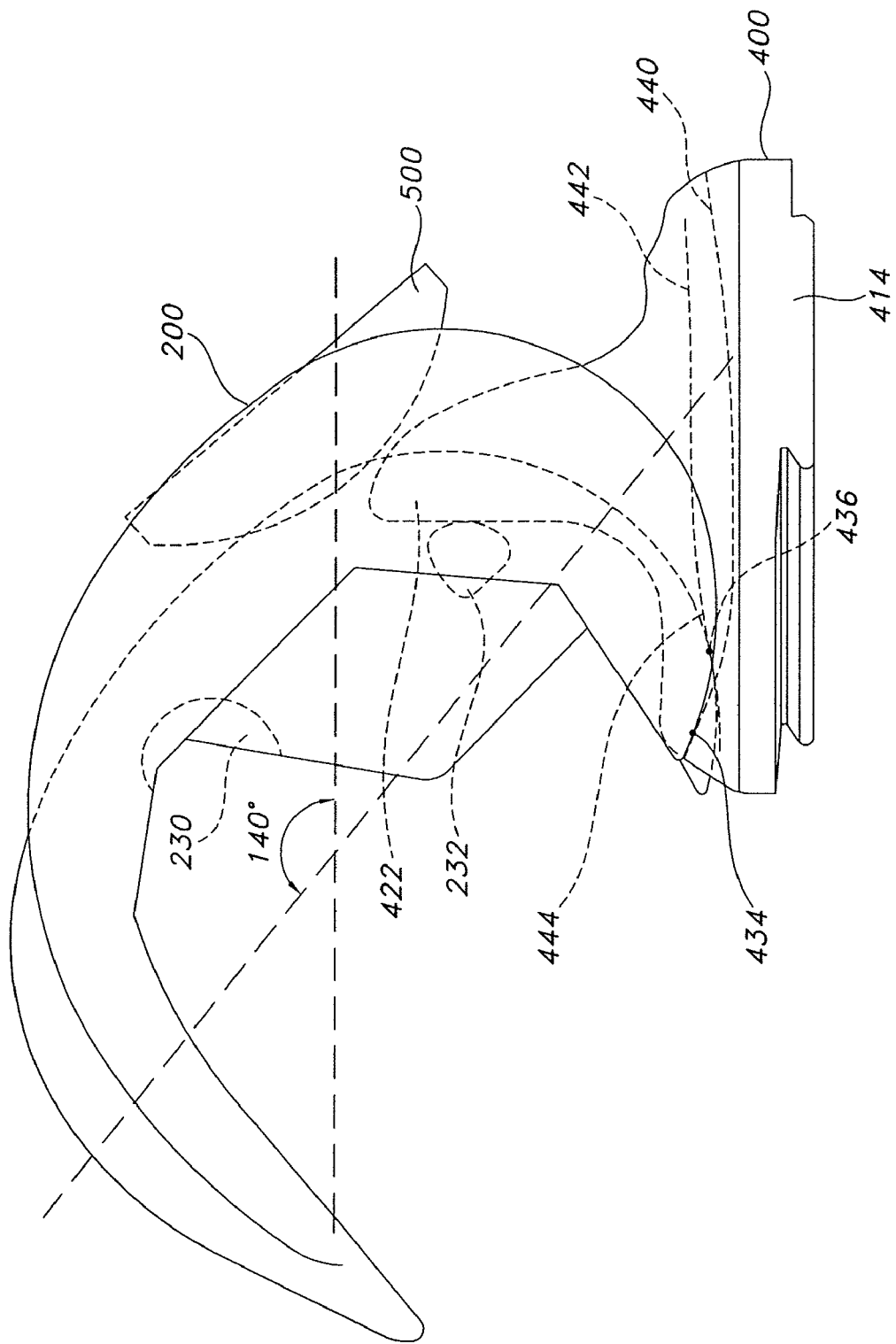
FIG. 10 is a side view of portions of a left knee prosthesis according to an embodiment of the invention showing the kinematics of the knee at 140° flexion.
Figure 11:
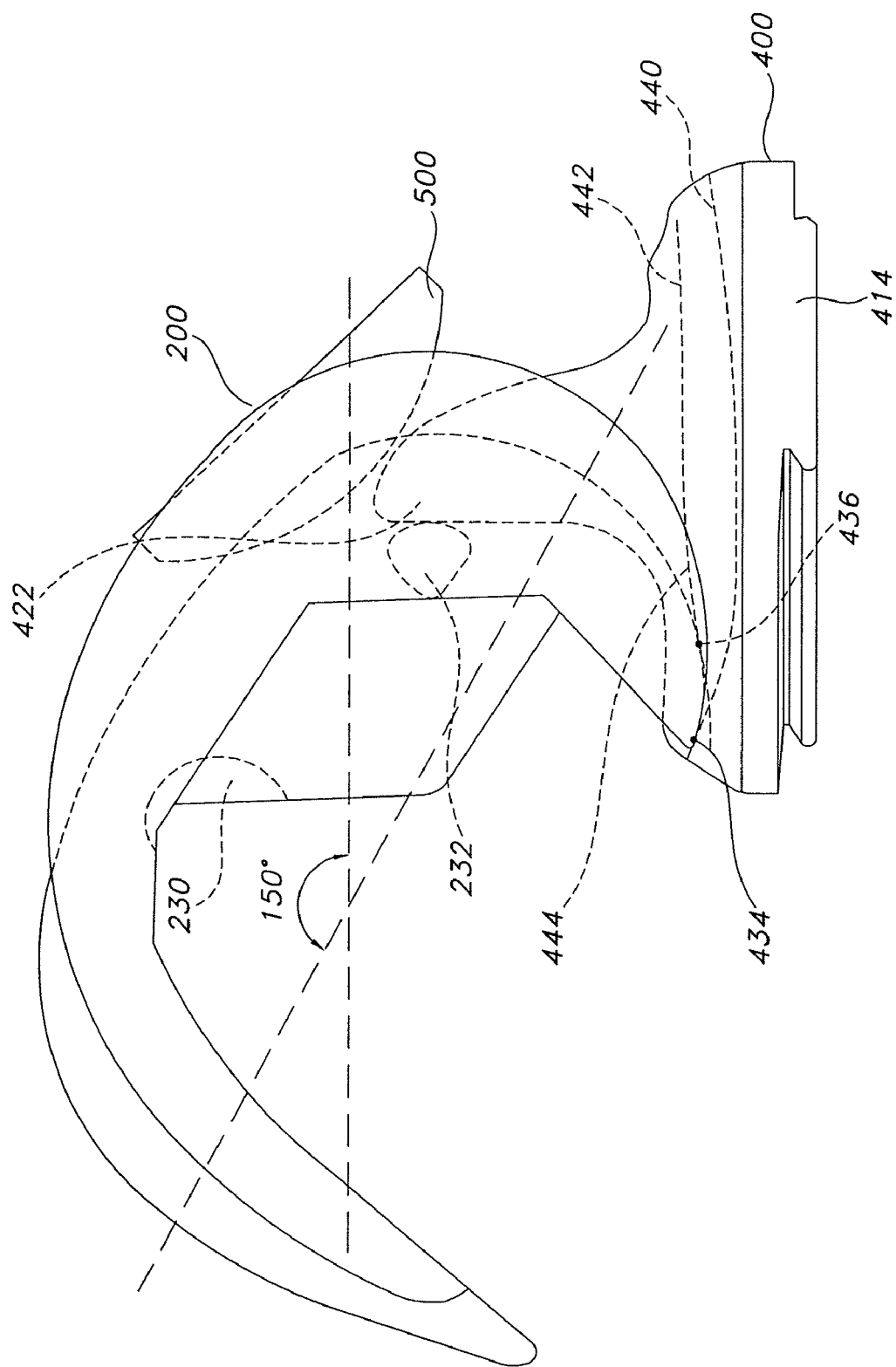
FIG. 11 is a side view of portions of a left knee prosthesis according to an embodiment of the invention showing the kinematics of the knee at 150° flexion.
Figure 12:
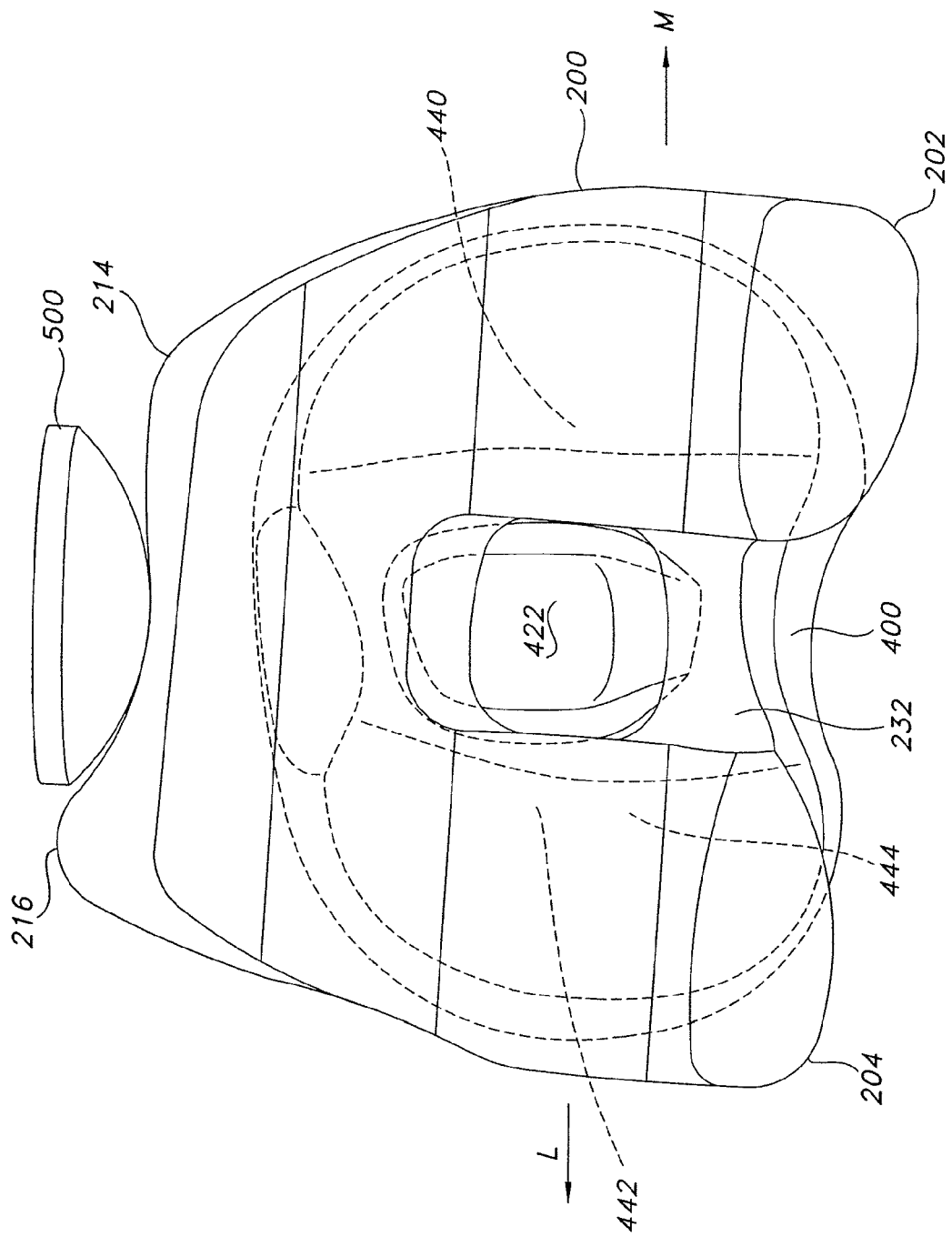
FIG. 12 is a top plan view of portions of a left knee prosthesis according to an embodiment of the invention showing the kinematics of the knee at full extension.
Figure 13:
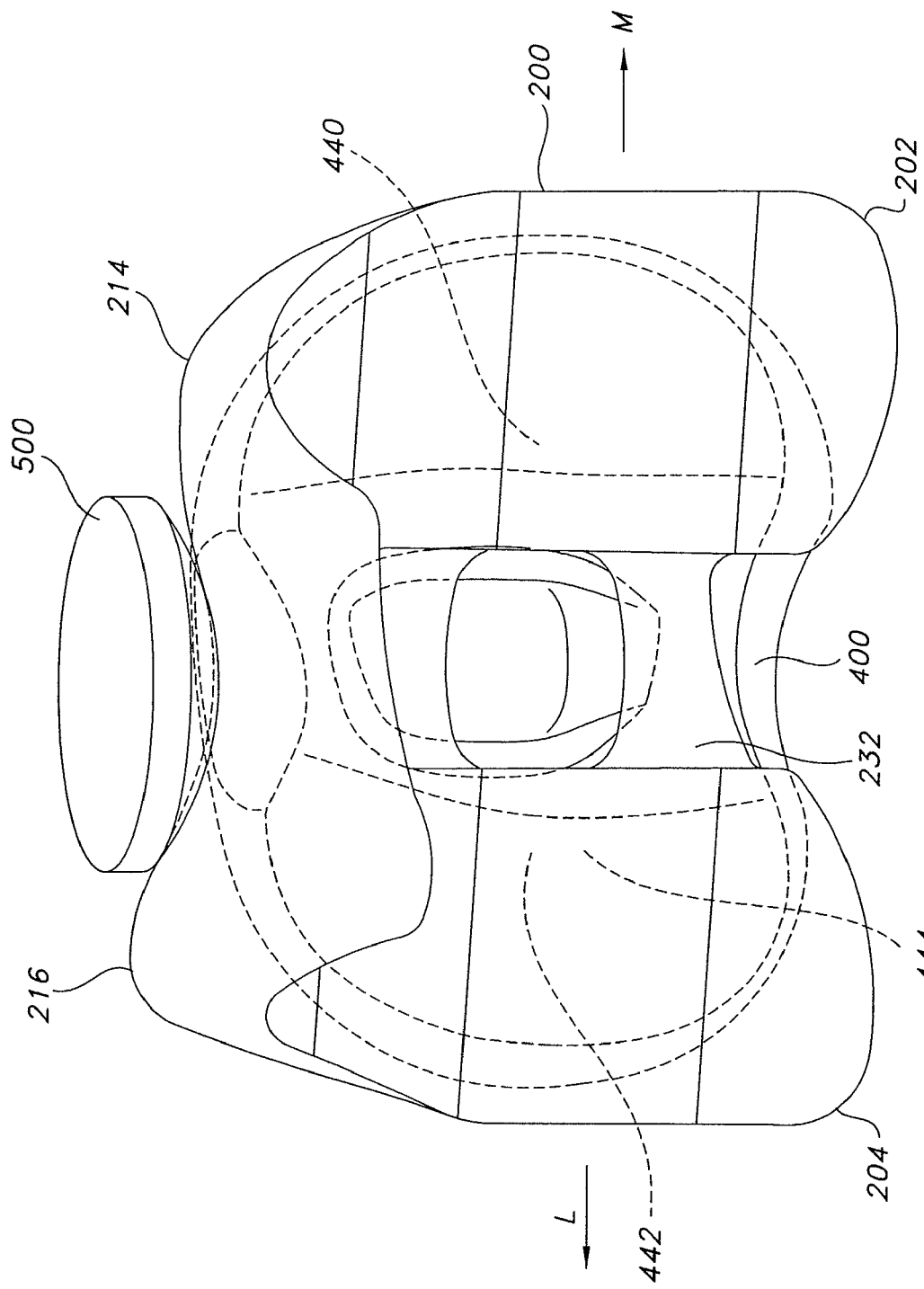
FIG. 13 is a top plan view of portions of a left knee prosthesis according to an embodiment of the invention showing the kinematics of the knee at 30° flexion.
Figure 14:
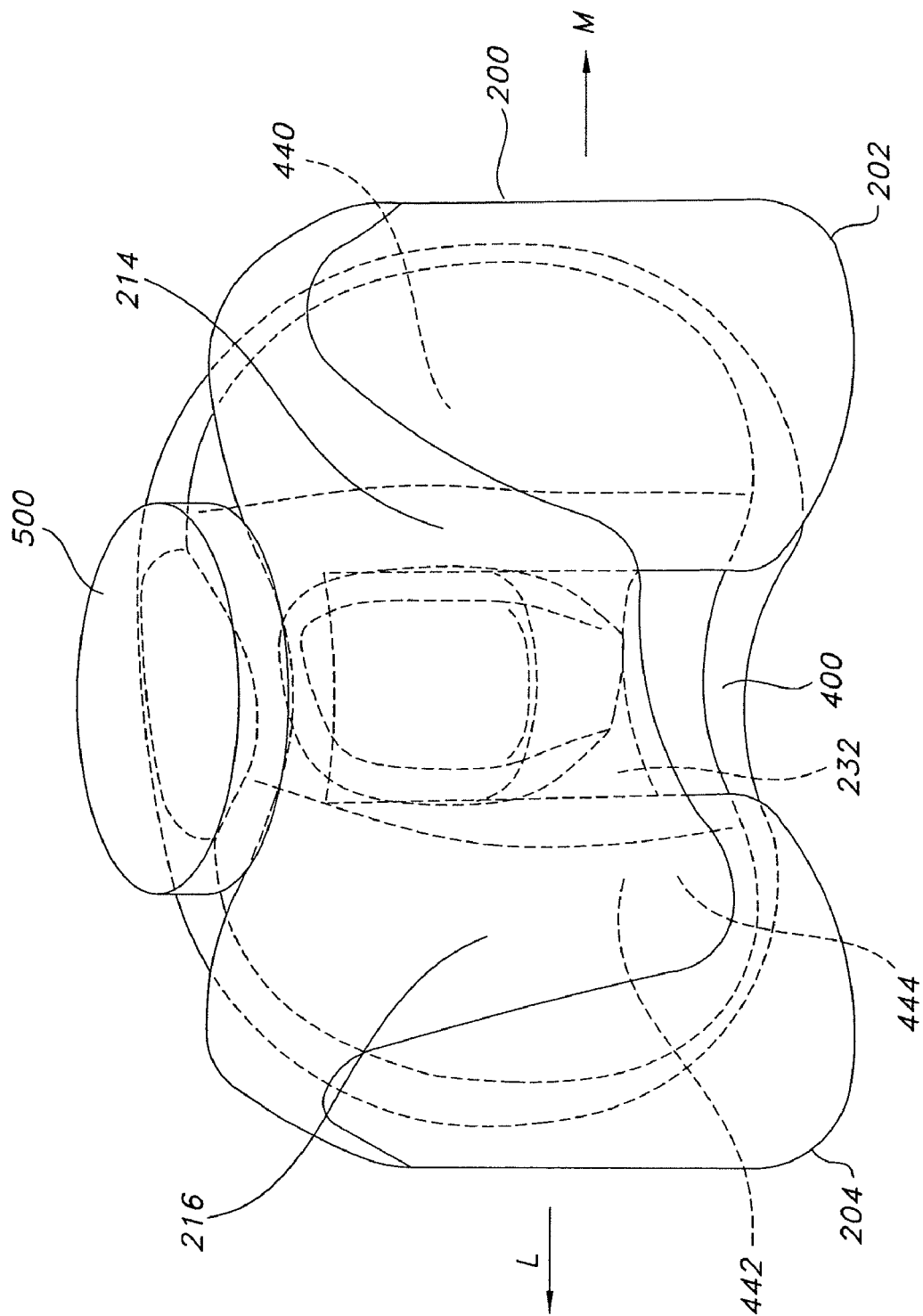
FIG. 14 is a top plan view of portions of a left knee prosthesis according to an embodiment of the invention showing the kinematics of the knee at 60° flexion.
Figure 15:
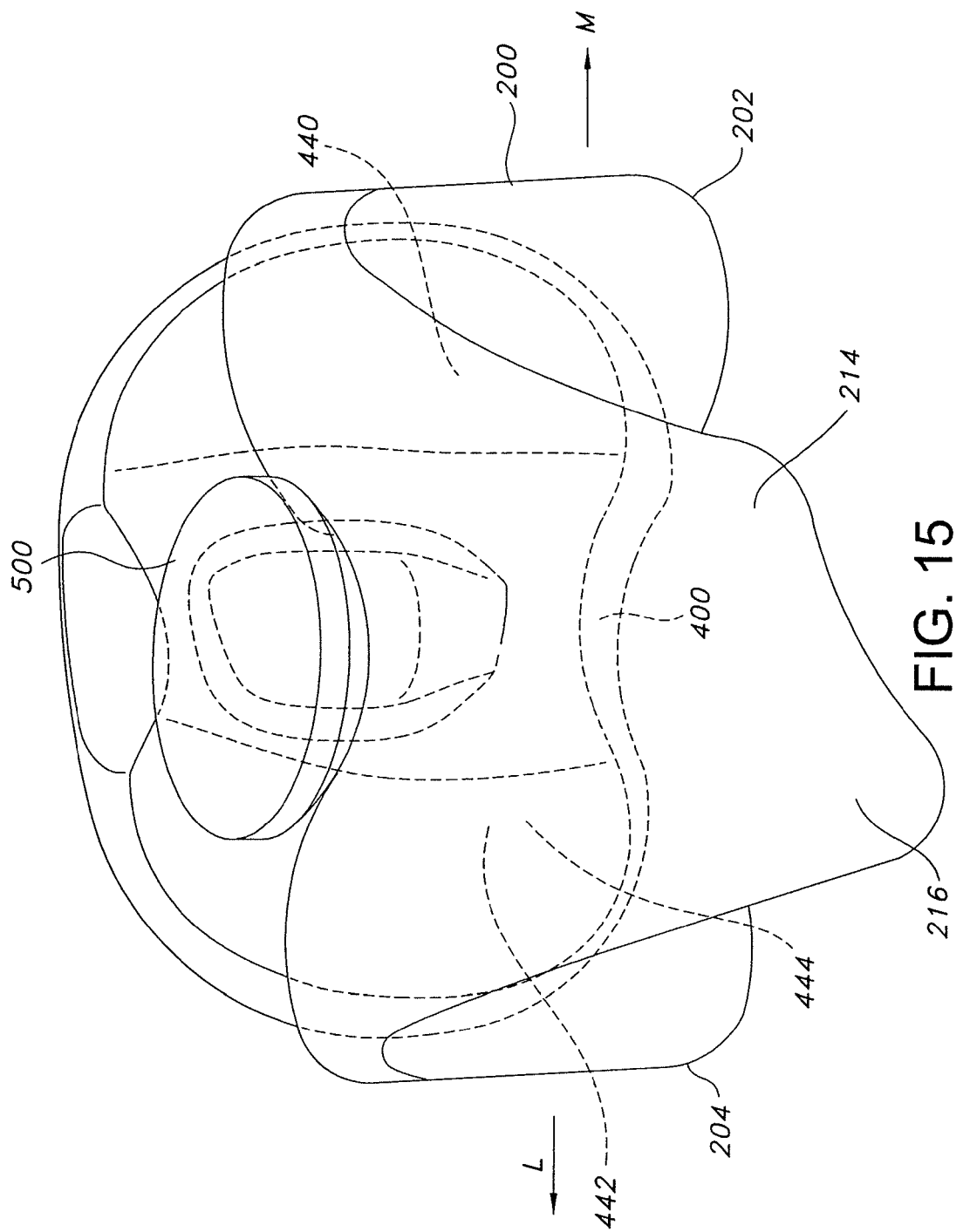
FIG. 15 is a top plan view of portions of a left knee prosthesis according to an embodiment of the invention showing the kinematics of the knee at 90° flexion.
Figure 16:
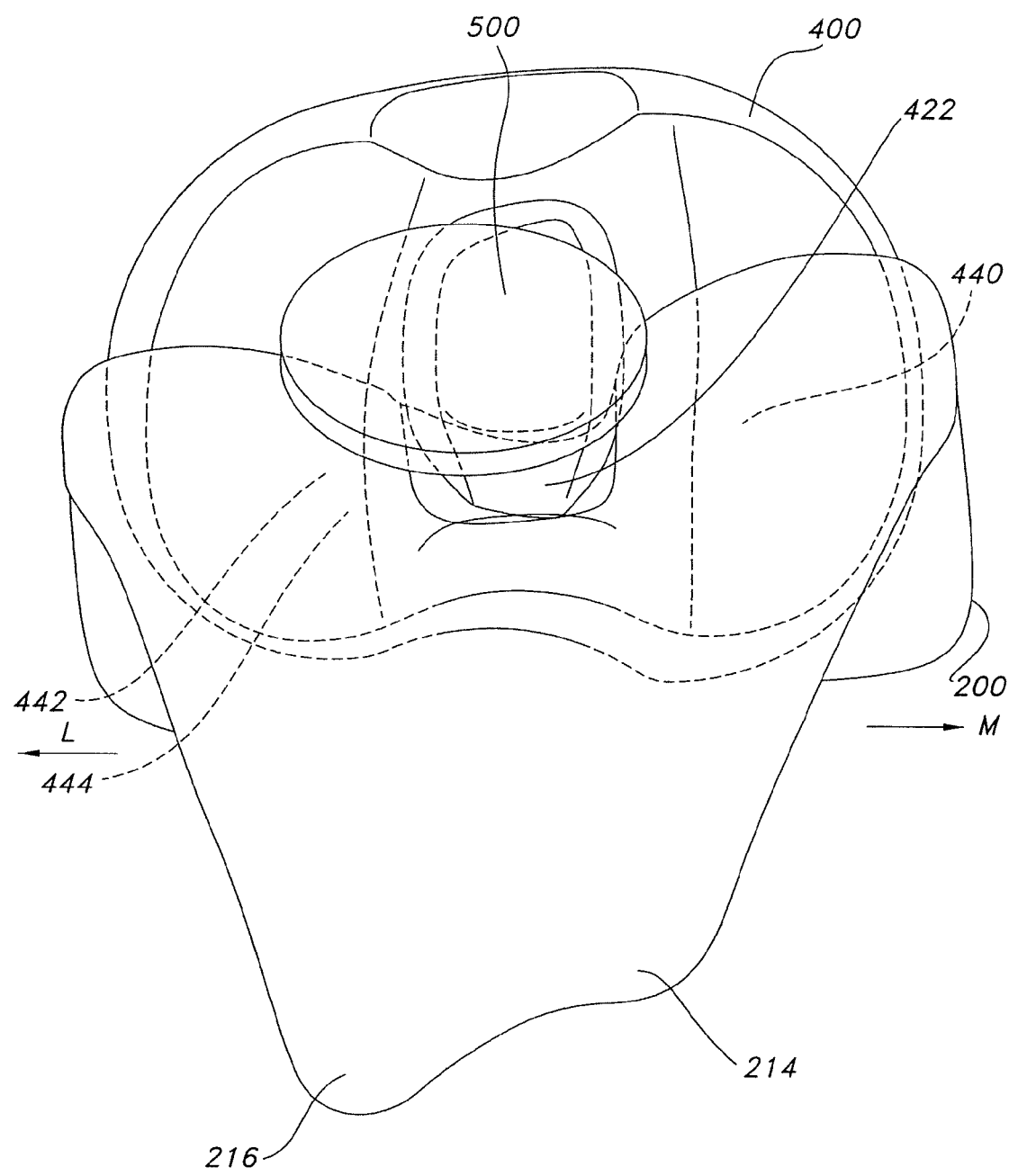
FIG. 16 is a top plan view of portions of a left knee prosthesis according to an embodiment of the invention showing the kinematics of the knee at 120° flexion.
Figure 17:
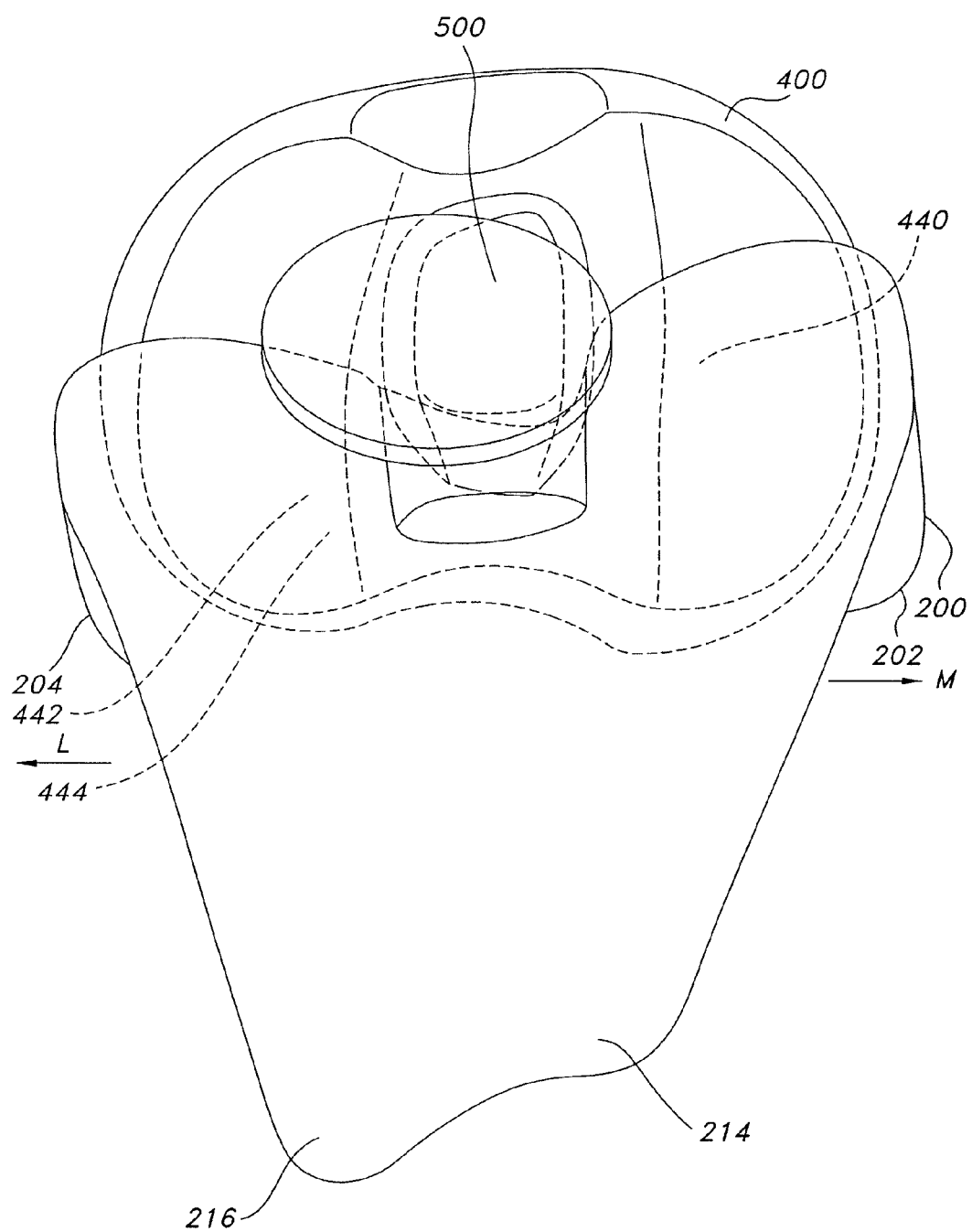
FIG. 17 is a top plan view of portions of a left knee prosthesis according to an embodiment of the invention showing the kinematics of the knee at 130° flexion.
Figure 18:
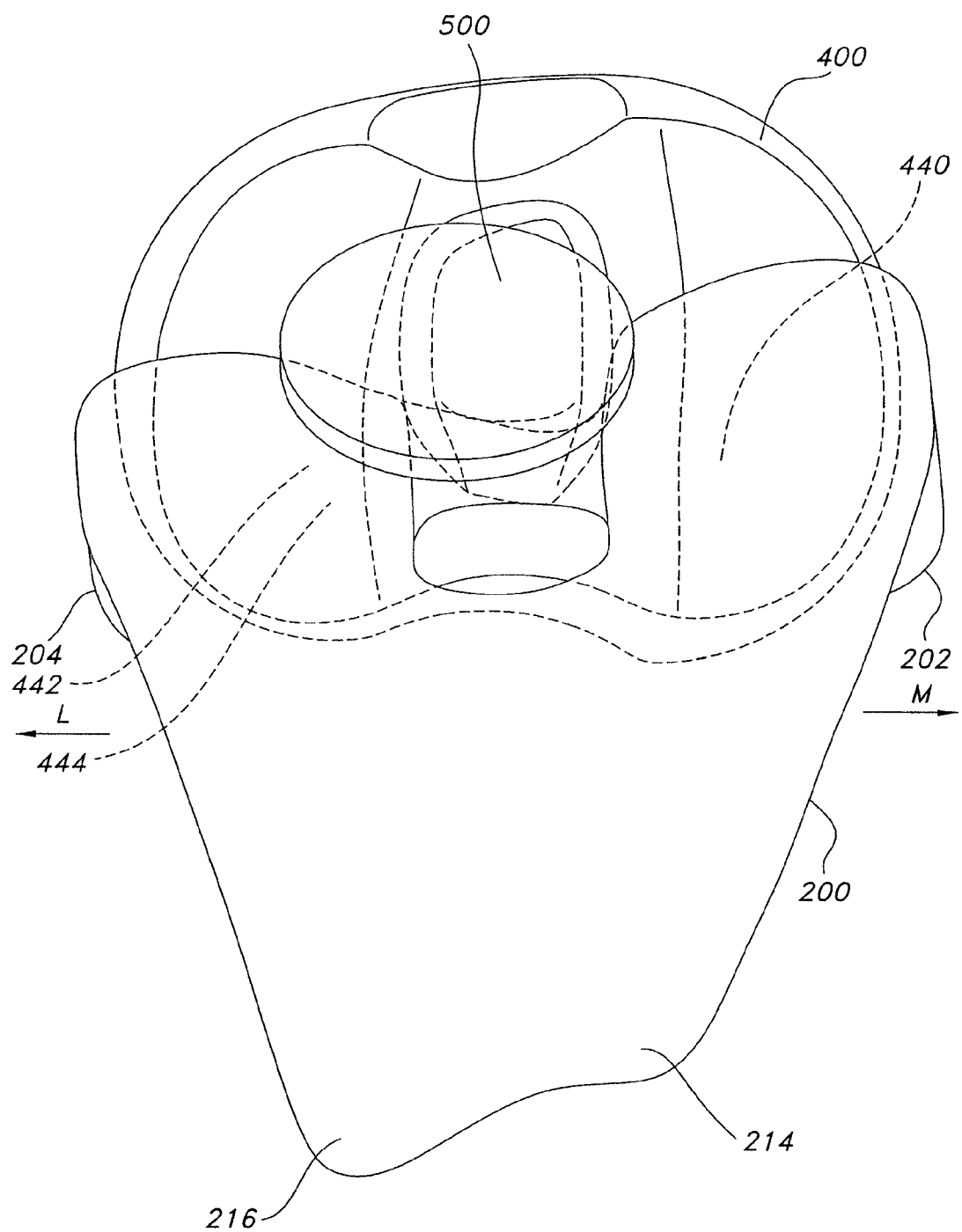
FIG. 18 is a top plan view of portions of a left knee prosthesis according to an embodiment of the invention showing the kinematics of the knee at 140° flexion.
Figure 19:
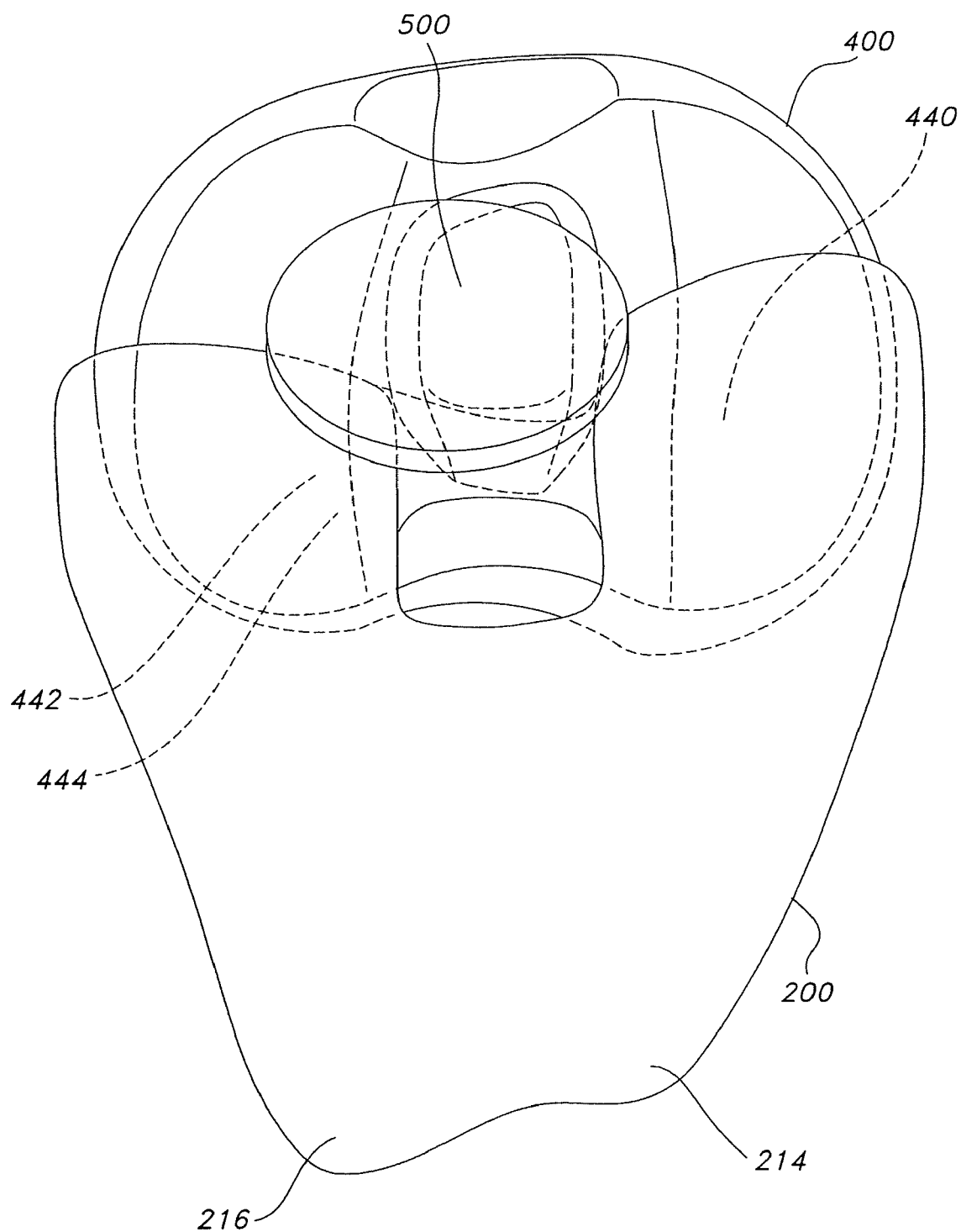
FIG. 19 is a top plan view of portions of a left knee prosthesis according to an embodiment of the invention showing the kinematics of the knee at 150° flexion.

This rotation, along with the increased flexion of the knee prostheses 100 of the invention, is evident in the series of side views of portions of a knee prosthesis 100 shown in FIGS. 4-11. To demonstrate the rotation between the femoral component 200 and the insert 400, which would be fixed on a tibial component 300 in a fully assembled knee prosthesis 100, the insert 400 shown remains stationary, as the femoral component 200 rotates substantially about the medial contact point. Thus, as shown in FIG. 4, the knee is fully extended. As the knee flexes to 90 degrees (shown in FIG. 7), the lateral condylar section 204 of the femoral component 200 rotates posteriorly on the lateral side 416 of the insert 400. The rotation continues as the knee flexes to 130 degrees, as shown in FIG. 9, reaching at least approximately 8 degrees of internal rotation of the tibia relative to the femur. As the knee continues to flex beyond approximately 130 degrees, as shown in FIGS. 10-11, the internal rotation stays substantially the same, as the relative motion is primarily posterior translation of the femoral component on the insert.

As the drawings show, when the knee prosthesis 100 is assembled, the central post or raised portion of the insert 400 fits within the intercondylar recess. Because the femoral component 200 and the insert 400 are not fastened to each other, the femoral component 200 is able to easily articulate on the insert 400.

Figure 6:
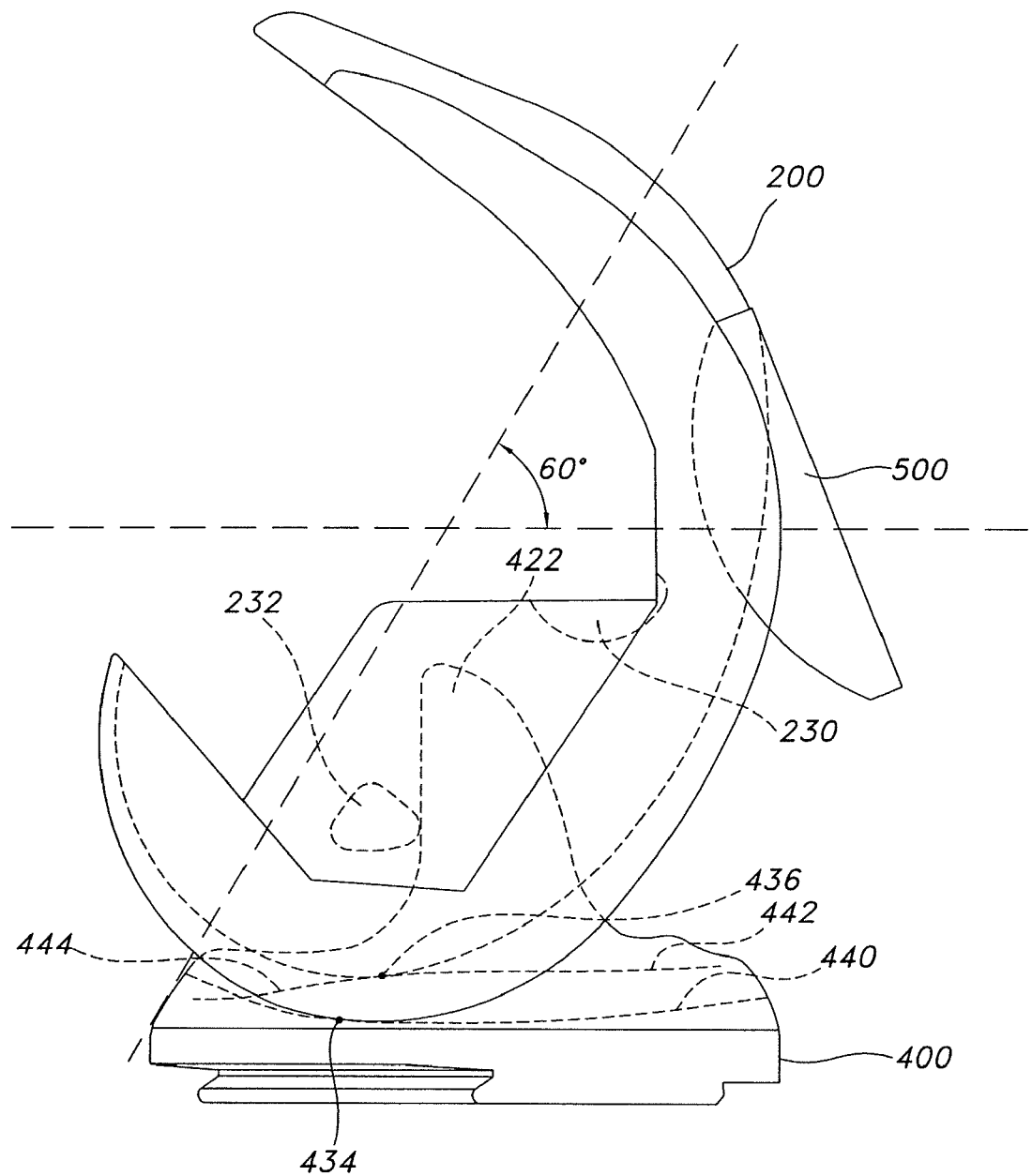
FIG. 6 is a side view of portions of a left knee prosthesis according to an embodiment of the invention showing the kinematics of the knee at 60° flexion.
Figure 7:
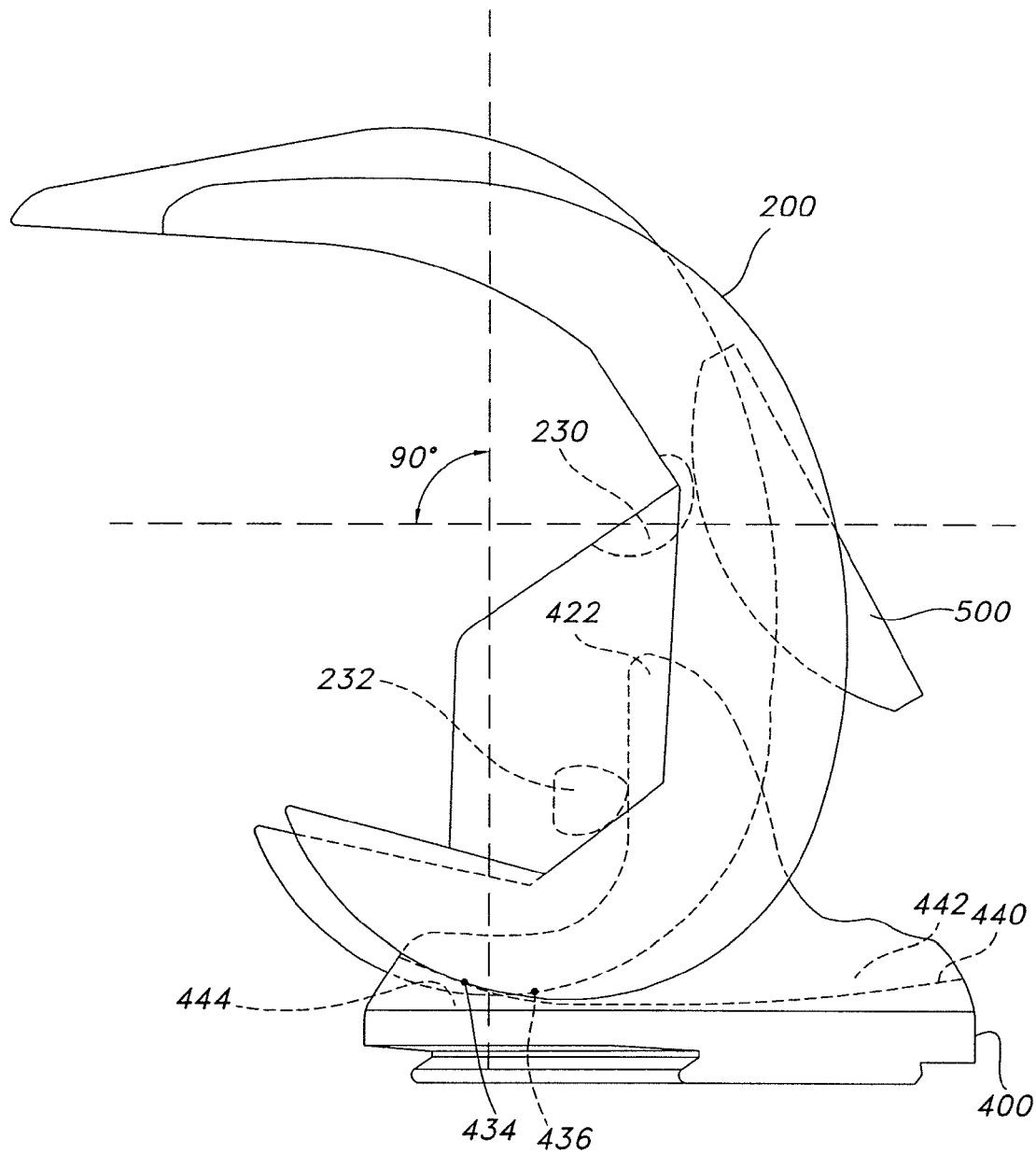
FIG. 7 is a side view of portions of a left knee prosthesis according to an embodiment of the invention showing the kinematics of the knee at 90° flexion.
Figure 8:
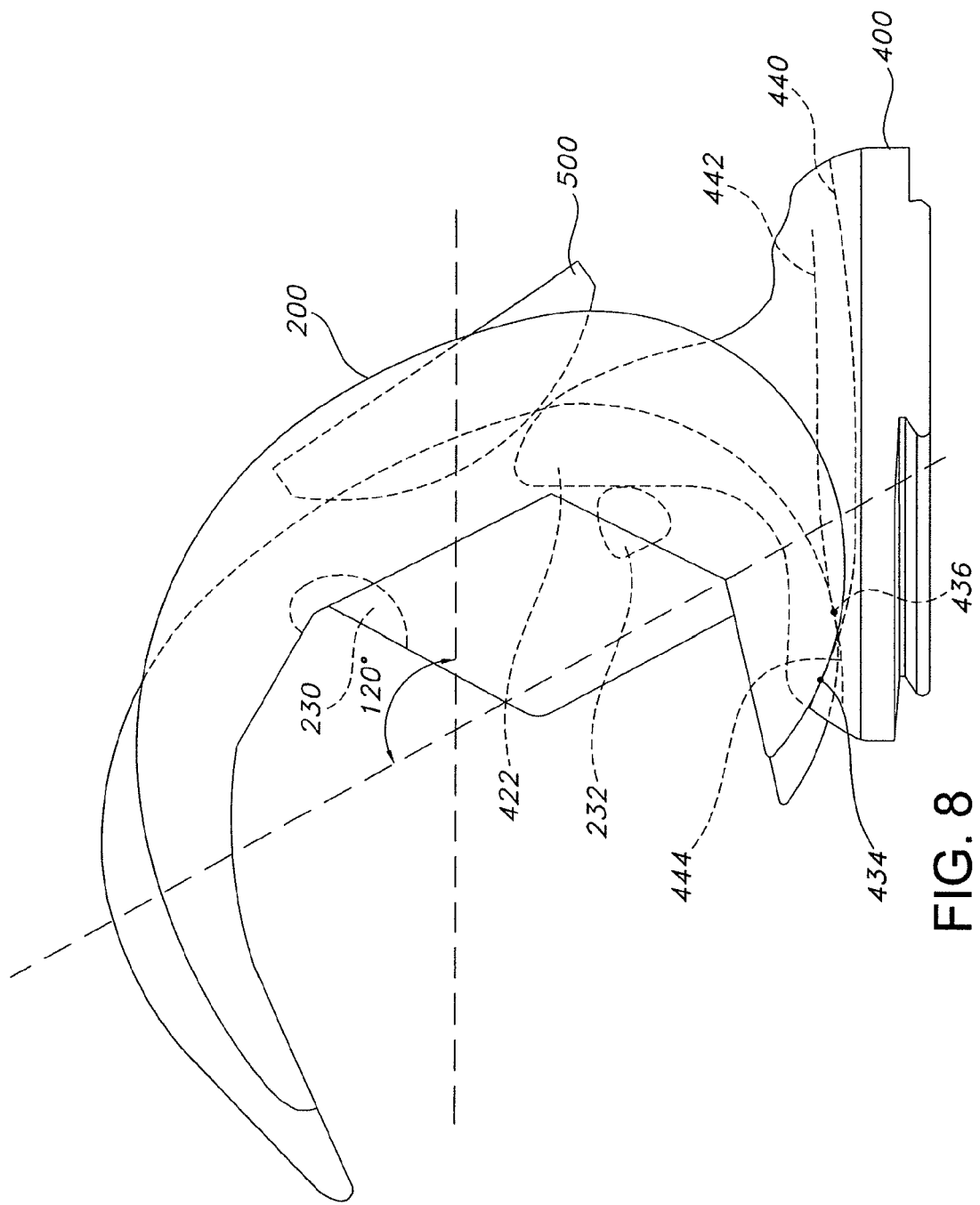
FIG. 8 is a side view of portions of a left knee prosthesis according to an embodiment of the invention showing the kinematics of the knee at 120° flexion.

FIGS. 4-11 thus sequentially show, from a side cross sectional aspect, kinematics of components of a knee prosthesis according to a preferred embodiment of the invention. FIGS. 12-19 show the same kinematics from a plan aspect, looking "down" on the prosthesis. These figures show kinematics of the prosthesis components at flexion angles of 0, 30, 60, 90, 120, 130, 140, and 150 degrees, respectively. At flexion angles of approximately 50 to 60 degrees, the cam 232 begins contacting the post 422 for posterior stabilization, as shown in FIG. 6. As the rotation of the femoral component 200 continues, the patella implant 500 moves down the trochlear groove 206, which is structured according to aspects of the invention to simulate natural anatomy in order to allow the patella implant 500 to track properly, and generally from a lateral to medial position relative to the femoral component 200 as flexion continues. In this fashion, the shape of the femoral component accommodates the natural action of the kneecap as a fulcrum on the knee joint for the considerable forces applied by the quadriceps and the patellar ligament. As the knee flexes from substantially zero degrees of flexion to substantially 130 degrees of flexion, the tibial rotation inducing surface 444 of the particular (nonlimiting) structure shown in the drawings acting in combination with the lateral condylar section 204, plus the action of the asymmetrical posterior cam 232 of the femoral component 200 on the post 422 of the insert, impart inward rotation to the insert 400 relative to the femur. This inward rotation corresponds to such inward rotation in the normal knee, and allows, among other things, the lower leg to be "folded" inward relative to the upper leg so that the patellar ligament and tendons from the quadriceps are not forced to be extended over the lateral part of the knee as is the case in some conventional designs. Yet the structure of the components shown in these drawings allows such natural internal rotation and other natural articulation of the tibia and femur relative to each other without freeing rotation of the insert relative to the tibial implant, or freeing other components in the prosthesis to move relative to each other, thereby taxing the other, weaker ligaments and tendons forming part of the knee, which are required to assume the new task of restraining the freed prosthetic components.

Designs more closely approximating the structure and/or operation of the natural knee may be carried out according to the present invention by considering forces acting on the knee that are of more considerable magnitude than other forces. For instance, 6 major forces on the tibia can be used to simulate what a natural knee experiences during certain activities such as walking: (1) ground reaction force which can range from some part up to multiples of body weight in a normal knee kinetic environment; (2) tension imposed by the quadriceps acting through the patella tendon in a generally proximal direction tending to proximal-posterior in flexion and to proximal-anterior in extension; (3) tension applied by the hamstrings in a generally posterior direction; (4, 5) contact force of each condyle on its corresponding bearing surface of the tibial plateau; and (6) posterior stabilization force imposed by the posterior cruciate ligament or insert on the femur. The inventors have recognized that reducing the myriad of forces acting on the knee (such as from various more minor tendons and ligaments) to a manageable number, which may increase as time and processing power continue to evolve, allows for reliable and effective testing of proposed knee prosthesis designs, by accurately simulating what real knees experience. This manageable set of conditions may be combined with information that is known about the structure and the kinematics of natural knees to impose an essentially realistic test regime for computer testing and development of acceptable knee prosthetic designs.

Applying a testing regime using a manageable but essentially realistic set of conditions allows iterative proposal of a design, testing it for performance in virtual, automated fashion in a computer, modification of the proposed design to reduce negative performance characteristics and to enhance positive ones, and repeated iteration of these tasks until an acceptable design is reached. The developers may therefore accordingly proceed at least partially iteratively, using test conditions that simulate what a real knee joint experiences and how it performs in such an environment, rather than attempting to design the complicated knee prosthetic components in a deterministic fashion based on anecdotal information, observation of knee components being articulated in the operating room, or based on assumptions that can be static and not reflect the complexity of nature.

The foregoing is provided for disclosure of various embodiments, aspects and structures relating to the invention. Various modifications, additions and deletions may be made to these embodiments and/or structures without departing from the scope and spirit of the invention.

The invention claimed is:

1. A knee prosthesis comprising a femoral component configured to fit on a distal end of a resected femur, the femoral component comprising:
   an anterior portion comprising (i) an anterior portion planar interior surface configured to interface with the resected femur and (ii) an anterior portion exterior surface opposite the anterior portion planar interior surface, the anterior portion exterior surface including a trochlear groove;
   a lateral condyle section comprising a posterior portion which in turn comprises (i) a lateral condyle section posterior portion planar interior surface configured to interface with the resected femur and (ii) a lateral condyle section posterior portion exterior surface opposite the lateral condyle section posterior portion planar interior surface, the lateral condyle section posterior portion exterior surface comprising a posterior-lateral articular surface; and
   a medial condyle section comprising (i) a posterior portion which in turn comprises a medial condyle section posterior portion planar interior surface configured to interface with the resected femur and (ii) a medial condyle section posterior portion exterior surface opposite the medial condyle section posterior portion planar interior surface, the medial condyle section posterior portion exterior surface comprising a posterior-medial articular surface;
   wherein a plane formed by the anterior portion planar interior surface converges proximally with a plane formed by the lateral condyle section posterior portion planar interior surface or a plane formed by the medial condyle section posterior portion planar interior surface.

2. The knee prosthesis of claim 1, wherein the lateral condyle section and the medial condyle section comprise a distal portion which in turn comprises a condyle section distal portion planar interior surface.

3. The knee prosthesis of claim 2, wherein the condyle section distal portion planar interior surface forms an angle that is less than 90° relative to the medial condyle section posterior portion planar interior surface and the lateral condyle section posterior portion planar interior surface.

4. The knee prosthesis of claim 1, wherein the plane formed by the anterior portion planar interior surface converges with both the plane formed by the lateral condyle section posterior portion planar interior surface and the plane formed by the medial condyle section posterior portion planar interior surface.

5. The knee prosthesis of claim 4, wherein the planes formed by the lateral condyle section posterior portion planar interior surface and the medial condyle section posterior portion planar interior surface are coplanar and converge with the plane formed by the anterior portion planar interior surface at a convergence angle of between 1 and 30 degrees.

6. The knee prosthesis of claim 4, wherein the planes formed by the lateral condyle section posterior portion planar interior surface and by the medial condyle section posterior portion planar interior surface are coplanar and converge with the plane formed by the anterior portion planar interior surface at a convergence angle of 15 degrees.

7. The knee prosthesis of claim 4, wherein the lateral condyle section posterior portion planar interior surface and the medial condyle section posterior portion planar interior surface are not coplanar.

8. The knee prosthesis of claim 1, further comprising:
a tibial component configured to fit on a proximal end of a resected tibia; and
a third structure configured to fit between the femoral component and the tibial component.

9. The knee prosthesis of claim 1, wherein the anterior portion comprises a second anterior portion planar interior surface.

10. A knee prosthesis comprising a femoral component configured to fit on a distal end of a resected femur, the femoral component comprising:
an anterior portion comprising (i) an anterior portion planar interior surface configured to interface with the resected femur and (ii) an anterior portion exterior surface opposite the anterior portion planar interior surface, the anterior portion exterior surface including a trochlear groove;
a lateral condyle section comprising a posterior portion which in turn comprises a lateral condyle section posterior portion planar interior surface configured to interface with the resected femur, wherein the lateral condyle section posterior portion planar interior surface (i) comprises a proximal portion and a distal portion and (ii) is opposite a lateral condyle section posterior portion exterior surface, which comprises a posterior-lateral articular surface; and
a medial condyle section comprising a posterior portion which in turn comprises a medial condyle section posterior portion planar interior surface configured to interface with the resected femur, wherein the medial condyle section posterior portion planar interior surface comprises a proximal portion and a distal portion and (ii) is opposite a medial condyle section posterior portion exterior surface, which comprises a posterior-medial articular surface;
wherein the proximal portion of the lateral condyle section posterior portion planar interior surface is located closer to a plane formed by the anterior portion planar interior surface than is the distal portion of the lateral condyle section posterior portion planar interior surface; and
wherein the proximal portion of the medial condyle section posterior portion planar interior surface is located closer to a plane formed by the anterior portion planar interior surface than is the distal portion of the medial condyle section posterior portion planar interior surface.

11. The knee prosthesis of claim 10, further comprising:
a tibial component configured to fit on a proximal end of a resected tibia; and
a third structure configured to fit between the femoral component and the tibial component.

12. The knee prosthesis of claim 10, wherein a plane formed by the lateral condyle section posterior portion planar interior surface and a plane formed by the medial condyle section posterior portion planar interior surface are coplanar and converge with a plane formed by the anterior portion planar interior surface at a convergence angle of between 1 and 30 degrees.

13. The knee prosthesis of claim 10, wherein a plane formed by the lateral condyle section posterior portion planar interior surface and a plane formed by the medial condyle section posterior portion planar interior surface are coplanar and converge with a plane formed by the anterior portion planar interior surface at a convergence angle of 15 degrees.

14. The knee prosthesis of claim 10, wherein the lateral condyle section posterior portion planar interior surface and the medial condyle section posterior portion planar interior surface are not coplanar.

15. The knee prosthesis of claim 10, wherein the anterior portion comprises a second anterior portion planar interior surface.

16. A knee prosthesis comprising a femoral component configured to fit on a distal end of a resected femur, the femoral component comprising:
an anterior portion comprising an anterior portion planar interior surface configured to interface with the resected femur;
a lateral condyle section comprising a posterior portion which in turn comprises a lateral condyle section posterior portion planar interior surface configured to interface with the resected femur; and
a medial condyle section comprising a posterior portion which in turn comprises a medial condyle section posterior portion planar interior surface configured to interface with the resected femur;
wherein a plane formed by the lateral condyle section posterior portion planar interior surface and a plane formed by the medial condyle section posterior portion planar interior surface are coplanar and converge with a plane formed by the anterior portion planar interior surface at a convergence angle of between 1 and 30 degrees to capture the resected femur and such that they are configured to allow the femoral component to be rotated onto the resected femur.

17. The knee prosthesis of claim 16, further comprising:
a tibial component configured to fit on a proximal end of a resected tibia; and
a third structure configured to fit between the femoral component and the tibial component.

18. The knee prosthesis of claim 16, wherein a plane formed by the lateral condyle section posterior portion planar interior surface and a plane formed by the medial condyle section posterior portion planar interior surface are coplanar and converge with a plane formed by the anterior portion planar interior surface at a convergence angle of 15 degrees.

19. The knee prosthesis of claim 16, wherein the lateral condyle section posterior portion planar interior surface and the medial condyle section posterior portion planar interior surface are not coplanar.

20. The knee prosthesis of claim 16, wherein the anterior portion comprises a second anterior portion planar interior surface.

21. A knee prosthesis comprising a femoral component configured to fit on a distal end of a resected femur, the femoral component comprising:
- an anterior portion comprising an anterior portion planar interior surface configured to interface with the resected femur;
- a lateral condyle section comprising a posterior portion which in turn comprises (i) a lateral condyle section posterior portion planar interior surface configured to interface with the resected femur and (ii) a lateral condyle section posterior portion exterior surface opposite the lateral condyle section posterior portion planar interior surface, the lateral condyle section posterior portion exterior surface comprising a posterior-lateral articular surface; and
- a medial condyle section comprising a posterior portion which in turn comprises (i) a medial condyle section posterior portion planar interior surface configured to interface with the resected femur and (ii) a medial condyle section posterior portion exterior surface opposite the medial condyle section posterior portion planar interior surface, the medial condyle section posterior portion exterior surface comprising a posterior-medial articular surface;
- wherein the medial condyle section posterior portion planar interior surface and the lateral condyle section posterior portion planar interior surface are backdrafted toward the anterior portion planar interior surface wherein the anterior portion planar interior surface converges proximally toward the medial and lateral condyle section posterior portion planar interior surfaces.

22. The knee prosthesis of claim 21, further comprising:
- a tibial component configured to fit on a proximal end of a resected tibia; and
- a third structure configured to fit between the femoral component and the tibial component.

23. The knee prosthesis of claim 21, wherein a plane formed by the lateral condyle section posterior portion planar interior surface and a plane formed by the medial condyle section posterior portion planar interior surface are coplanar and converge with a plane formed by the anterior portion planar interior surface at a convergence angle of between 1 and 30 degrees.

24. The knee prosthesis of claim 21, wherein planes formed by the lateral condyle section posterior portion planar interior surface and by the medial condyle section posterior portion planar interior surface are coplanar and converge with the plane formed by the anterior portion planar interior surface at a convergence angle of 15 degrees.

25. The knee prosthesis of claim 21, wherein the lateral condyle section posterior portion planar interior surface and the medial condyle section posterior portion planar interior surface are not coplanar.

26. The knee prosthesis of claim 21, wherein the anterior portion comprises a second anterior portion planar interior surface.

27. A knee prosthesis comprising a femoral component adapted to fit on a distal end of a femur, the femoral component including:
- an anterior portion which includes an interior surface adapted to interface with the femur;
- a lateral condylar structure which includes a posterior section which in turn includes an interior surface adapted to interface with the femur; and
- a medial condylar structure which includes a posterior section which in turn includes an interior surface adapted to interface with the femur;
- wherein the interior surfaces are adapted to physically capture at least a portion of the femur in the femoral component relative to a distal translation substantially parallel to an anatomic axis of the femur; and
- wherein the planes of the interior surfaces of the condylar structure posterior sections converge with the plane of the interior surface of the anterior portion at an angle of between substantially 1 and 30 degrees to allow the femoral component to clear resected portions of the femur physically as the femoral component is rotated onto the femur about posterior portions of the femur during installation.

28. A knee prosthesis according to claim 27 further comprising:
- a tibial component adapted to fit on a proximal end of a tibia; and
- a third structure configured to fit between the femoral component and the tibial component.

29. A knee prosthesis according to claim 28 wherein:
- the geometry of the lateral condylar structure is different from the geometry of the medial condylar structure of the femoral component,
- the third structure includes a lateral proximal surface adapted to cooperate with the lateral condylar structure of the femoral component, and a medial proximal surface adapted to cooperate with the medial condylar structure of the femoral component, and
- the geometry of the lateral proximal surface and the medial proximal surface of the third structure differ in shape from each other, to assist in imparting internal rotation on the tibia relative to the femoral component as the knee flexes from substantially zero degrees of flexion to substantially 130 degrees of flexion.

30. A knee prosthesis according to claim 27 wherein the interior surfaces of the femoral component are substantially planar.

31. A knee prosthesis according to claim 30 wherein the interior surfaces of the condylar structure posterior sections are substantially coplanar with each other.

32. A knee prosthesis according to claim 30 wherein the planes of the interior surfaces of the condylar structure posterior sections converge with the plane of the interior surface of the anterior portion at an angle of substantially 15 degrees.

33. A knee prosthesis according to claim 27 wherein the interior surfaces of the condylar structure posterior sections are not parallel to the interior surface of the anterior portion.

* * * * *